US007592145B2

(12) United States Patent
Bao et al.

(10) Patent No.: US 7,592,145 B2
(45) Date of Patent: Sep. 22, 2009

(54) PIN 1 AS A MARKER FOR PROSTATE CANCER

(75) Inventors: Lere Bao, Newton, MA (US); Da Gong Wang, Chestnut Hill, MA (US)

(73) Assignee: Pintex Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 11/446,790

(22) Filed: Jun. 5, 2006

(65) Prior Publication Data

US 2006/0216764 A1 Sep. 28, 2006

Related U.S. Application Data

(63) Continuation of application No. 10/071,521, filed on Feb. 8, 2002, now abandoned.

(60) Provisional application No. 60/267,552, filed on Feb. 9, 2001, provisional application No. 60/347,546, filed on Jan. 10, 2002.

(51) Int. Cl.
*G01N 33/53* (2006.01)
(52) U.S. Cl. ............... 435/7.1; 530/350; 530/387.1
(58) Field of Classification Search ............... 435/7.1; 530/350, 387.1
See application file for complete search history.

(56) References Cited

U.S. PATENT DOCUMENTS

| 5,952,467 | A | 9/1999 | Hunter et al. |
| 5,972,697 | A | 10/1999 | Hunter et al. |
| 6,037,164 | A | 3/2000 | Au-Young |
| 6,462,173 | B1 | 10/2002 | Lu et al. |
| 6,596,848 | B1 | 7/2003 | Hunter et al. |
| 2003/0068626 | A1 | 4/2003 | Wang et al. |

FOREIGN PATENT DOCUMENTS

| WO | WO-97/17986 A1 | 5/1997 |
| WO | WO-99/63931 A2 | 12/1999 |
| WO | WO-01/38878 A2 | 5/2001 |
| WO | WO-02/065091 A2 | 8/2002 |

OTHER PUBLICATIONS

Tockman et al (Cancer Res., 1992, 52:2711s-2718s).*
Oesterreich, S et al, 1996 (Clin Cancer Res, 2: 1199-1206.*
Vandesompele J et al, 2003 (Oncogene, 22(3): 456-60).*
Bostwick et al, 1998, Cancer, 82: 2256-61.*
Montironi, Rodolfo et al., "Prostate-specific antigen as a marker of prostate disease," *Virchows. Arch.*, vol. 436:297-304 (2000).
Rippmann, Joerg F. et al., "Phosphorylation-dependent Proline Isomerization Catalyzed by Pin1 Is Essential for Tumor Cell Survival and Entry into Mitosis," *Cell Growth & Differentiation*, vol. 11:409-416 (2000).
European Search Report for Application No. 02724926.7-2402, dated Jul. 5, 2007.
American Urological Association, "Prostate-specific antigen (PSA) best practice policy," *Oncology*, vol. 14(2):1-19 (2000).
Ayala, Gustavo et al, "The Prolyl Isomerase Pin1 Is a Novel Prognostic Marker in Human Prostate Cancer," *Cancer Research*, vol. 63:6244-6251 (2003).
Bowie, J.U. et al, "Deciphering the message in protein sequences: tolerance to amino acid substitutions," *Science*, vol. 247(4948):1306-1310 (1990).
Burgess, Wilson H. et al, "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111:2129-2138 (1990).
Crenshaw, D.G., et al., "The mitotic peptidyl-prolyl isomerase, Pin1, interacts with Cdc25 and Plx1." *EMBO J.* Aug. 1998;17(5):1315-27.
Fischer, G., et al., "Nachweis einer enzymkatalyse für die cis-trans-isomerisierung der peptidbindung in prolinhaltigen peptiden." *Biomed. Biochim. Acta.* 1984; 43(10):1101-11.
Fischer, G., et al., "Peptidyl-prolyl *cis/trans* isomerases and their effectors" *Chem. Int. Ed. Engl.* 1994; 33:1415-36.
Garnick, M.B., "Prostate cancer: screening, diagnosis, and management." *Ann Intern Med.* May 1993;118(10):804-18.
Gillies, S.D. et al, "Antigen binding and biological activities of engineered mutant chimeric antibodies with human tumor specificities," *Hum. Antibodies Hybridomas*, vol. 1(1):47-54 (1990).
Herbert et al, The Dictionary of Immunology, Academic Press, 4th ed., p. 58 (1995).
Holmes, Eric H., "PSMA specific antibodies and their diagnostic and therapeutic use," *Expert Opinion on Investigational Drugs*, vol. 10(3):511-519 (2001).
Lazar, Eliane et al, "Transforming Growth Factor α: Mutation of Aspartic Acid 47 and Leucine 48 Results in Different Biological Activities," *Molecular and Cellular Biology*, vol. 8(3):1247-1252 (1988).
Lu, K.P., et al., "Properties and regulation of the cell cycle-specific NIMA protein kinase of *Aspergillus nidulans*." *The Journal of Biological Chemistry.* Apr. 1993;268(12):8769-76.
Lu, K.P., et al., "Evidence for a NIMA-like mitotic pathway in vertebrate cells." *Cell.* May 1995;81:413-24.

(Continued)

*Primary Examiner*—Larry R. Helms
*Assistant Examiner*—Minh-Tam Davis
(74) *Attorney, Agent, or Firm*—Lahive & Cockfield, LLP; Cynthia L. Kanik

(57) ABSTRACT

This invention provides methods for diagnosing prostate cancer, methods for measuring the aggressiveness of prostate cancer, and methods for identifying prostate cancer likely to metastasize. The diagnostic and prognostic assays of this invention include methods involving the antibody-based detection of Pin1 and the amplification of Pin1 RNA. The diagnostic and prognostic assays of this invention may be used in combination with other methods of prostate cancer diagnosis including the PSA test, digital rectal exam, and Gleason prostate tumor grading system.

8 Claims, 7 Drawing Sheets

OTHER PUBLICATIONS

Lu, K.P., et al., "A human peptidyl-prolyl isomerase essential for regulation of mitosis." *Nature*. Apr. 1996;380:544-7.

Lu, P.J., et al., "Function of WW domains as phosphoserine- or phosphothreonine-binding modules." *Science*. Feb. 1999;283(5406):1325-8.

Lu, P.J., et al., "The prolyl isomerase Pin1 restores the function of Alzheimer-associated phosphorylated tau protein." *Nature*. Jun. 1999; 399(6738):784-8.

Ranganathan, R., et al., "Structural and functional analysis of the mitotic rotamase Pin1 suggests substrate recognition is phosphorylation dependent." *Cell*. Jun. 1997; 89:875-86.

Roitt et al, Immunology, 4th ed., Mosby, London, pp. 7.7-7.8 (1998).

Schutkowski, M., et al., "Inhibition of peptidyl-prolyl *cis/trans* isomerase activity by substrate analog structures: thioxo tetrapeptide-4-nitroanilides." *Biochemistry*. 1995; 34:13016-26.

Shen, M., et al., "The essential mitotic peptidyl-prolyl isomerase Pin1 binds and regulates mitosis-specific phosphoproteins." *Genes Dev*. Mar. 1998; 12(5):706-20.

Tao, M.H. et al, "Studies of aglycosylated chimeric mouse-human IgG. Role of carbohydrate in the structure and effector functions mediated by the human IgG constant region," *J. Immunol.*, vol. 143(8):2595-2601 (1989).

Yaffe, M.B., et al., "Sequence-specific and phosphorylation-dependent proline isomerization: a potential mitotic regulatory mechanism," *Science*. Dec. 1997;278:1957-60.

Yaffe, M.B., et al., "The structural basis for 14-3-3: phosphopeptide binding specificity" *Cell*. Dec. 1997; 91:961-71.

Zhou, X.Z., et al., "Phosphorylation-dependent prolyl isomerization: a novel signaling regulatory mechanism." *Cell Mol Life Sci*. Nov. 1999; 56(9-10):788-806.

\* cited by examiner

Multivariate Analysis for PIN 1 as a Marker of Biochemical Recurrence in Gleason 6 and 7 Patients

| Models | | HR (95%CI) | | p-value |
|---|---|---|---|---|
| Univariate PIH (split at 100) | 2.642( | 1.554, | 4.493) | 0.0356 |
| Mulivariate PIH (split at 100) | 3.413( | 1.694, | 6.875) | 0.0006 |
| LN | 3.859( | 2.125, | 7.01) | <0.0001 |
| Margins | 4.121( | 2.513, | 6.757) | <0.0001 |
| SVI | 3.042( | 1.729, | 5.352) | 0.0001 |
| ECE | 2.490( | 1.356, | 4.542) | 0.0029 |
| UICC | 1.134( | 0.958, | 1.341) | 0.1431 |
| PreOpPSA | 1.015( | 1.002, | 1.027) | 0.0248 |

Visual PIN 1 Intensity High ("0" Vs ">0")

| Models | HR (95%CI) | | | p-value |
|---|---|---|---|---|
| Univariate PMIH (+/-) | 1.603 ( | 1.078, | 2.384 ) | 0.0198 |
| Mulivariate PMIH (+/-) | 1.941 ( | 1.255, | 3.001 ) | 0.0029 |
| LN | 2.912 ( | 1.011, | 4.600 ) | <0.0001 |
| Margins | 3.303 ( | 2.196, | 4.967 ) | <0.0001 |
| SVI | 2.706 ( | 1.714, | 4.272 ) | <0.0001 |
| Gleason | 2.151 ( | 1.619 | 2.860 ) | <0.0001 |
| ECE | 2.368 ( | 1.350, | 4.155 ) | 0.0027 |
| PreOpPSA | 1.025 ( | 1.014, | 1.036 ) | <0.0001 |

PIN 1 AS A MARKER FOR PROSTATE CANCER

RELATED APPLICATIONS

This application is a continuation of U.S. Ser. No. 10/071,521 filed Feb. 8, 2002 entitled "Pin1 as a Marker for Prostate Cancer", now abandoned, which claims priority to U.S. Provisional Application Ser. No. 60/267,552, filed Feb. 9, 2001 and U.S. Provisional Application Ser. No. 60/347,546, filed on Jan. 10, 2002, the entire contents of which are incorporated herein by this reference.

BACKGROUND OF THE INVENTION

The increased number of cancer cases reported in the United States, and, indeed, around the world, is a major concern. Currently there are only a handful of treatments available for specific types of cancer, and these treatments require not only an early detection of the malignancy, but also a reliable assessment of the severity of the malignancy. Carcinoma of the prostate (PCA) is the most frequently diagnosed cancer in men in the United States, and is the second leading cause of male cancer deaths (Karp et al., 1996, *Cancer Res.* 56:5547-5556). Over 40,000 Americans are estimated to have died of PCA in 1995, and about 244,000 new cases of prostate cancer were detected (Cancer Facts and Figures—1995, *American Cancer Society, Inc.*, 1995) and these numbers have increased annually at an alarming rate. Further, the rate of appearance of prostate cancer in African-American men is 37% higher than for their white counterparts (Jaroff, L. (Apr. 1, 1996), *Time*).

An unusual challenge presented by prostate cancer is that most prostate tumors do not represent life threatening conditions. Projections from autopsy surveys indicate that as many as 11 million American men have prostate cancer (Dhom, 1983, *J. Cancer Res. Clin. Oncol.*, 106:210-218). Cancer cells are generally found in the prostates of men who live into their seventies or eighties. However not all of these men develop prostate cancer (PCA), and autopsies show microscopic clusters of prostate cancer cells in one-third of men who die of other causes (Thayer, W., (Mar. 19, 1996), quoted in *Nutr. Act. Newsletter*, 23(2):12). Death rates from prostate cancer rise after age 55, and new cases of prostate cancer, are increasing even faster than the death rate. These figures are consistent with clinical observations of prostate carcinomas, which normally exhibit a slow and lingering course of progression. Such disease progression results in relatively few prostate tumors developing into cases of clinical concern during the lifetime of the patient. If, upon detection with available methods, the cancer appears well-differentiated, organ-confined and focal, treatment normally cannot extend the life expectancy of older patients.

Unfortunately, prostate carcinomas that are progressive in nature frequently have already metastasized by the time of clinical detection with available methods. Survival rates for individuals with metastatic prostate cancer are quite low. Between these two extremes are patients with prostate tumors that will metastasize during their lifetimes, but have not yet done so. For these patients, surgical removal of the prostate is curative and extends life expectancy. Therefore, accurate determination of which group a newly diagnosed patient falls into is critical in determining optimal treatment and patient survival.

The current primary diagnostic tool for disorders of the prostate is measurement of the level of prostate-specific antigen (PSA) in blood, which in normal men ranges from 0 to 4 nanograms/milliliters. The presence of Prostate Specific Antigen (PSA) can be measured with relative ease from blood samples using standard antibody-based detection kits. Prostate enlargement, a condition known as benign prostatic hyperplasia (BPH), is found in about half of men over age 45. With BPH, PSA levels rise in proportion to prostate size, possibly obscuring diagnosis of PCA. In addition, a significant proportion of men with PCA have normal PSA levels. The PSA test is somewhat non-specific for distinguishing PCA and BPH, and produces a degree of false negative results (Garnick, M., (1993), *Am. Inst. Med.*, 118:804-818). In the majority of cases, PSA elevation is due to BPH or prostatitis rather than carcinoma. The PSA test, a major advance over previous procedures, thus leaves much to be desired.

Although clinical and pathologic stage and histological grading systems (e.g., Gleason's) have been used to indicate prognosis for groups of patients based on the degree of tumor differentiation or the type of glandular pattern (Carter and Coffey, In: J. P. Karr and H. Yamanak (eds.), *Prostate Cancer: The Second Tokyo Symposium*, pp. 19-27, New York: Elsevier, 1989.; Diamond et al., *J. Urol.*, 128: 729-734, 1982), these systems do not adequately predict the progression rate of the cancer. While the use of computer-system image analysis of histologic sections of primary lesions for "nuclear roundness" has been suggested as an aide in the management of individual patients (Diamond et al., 1982, *J. Urol.*, 128: 729-734), this method is of limited use in studying the progression of the disease.

There currently is a need for new methods in the fight against prostate cancer and it would therefore be beneficial to provide specific methods and reagents for the diagnosis, staging, prognosis, and monitoring of prostate cancer.

SUMMARY OF THE INVENTION

This invention provides a method for facilitating the diagnosis of prostate cancer in a subject, comprising: assessing the level of Pin1 in a biological sample from the subject, wherein an elevation in the level of Pin1 is indicative of prostate cancer; and evaluating a TDPCA on the subject such that the diagnosis of prostate cancer is facilitated.

This invention also provides a method for facilitating the diagnosis of prostate cancer in a subject, comprising: assessing the level of Pin1 in a biological sample from the subject, wherein an elevation in the level of Pin1 is indicative of prostate cancer, and wherein the subject was previously categorized by a TDPCA as being likely but not certain to have prostate cancer.

In another aspect, this invention includes a method for measuring the aggressiveness of prostate cancer in a subject, comprising assessing the level of Pin1 in a biological sample from the subject, wherein an elevation in the level of Pin1 is indicative of the aggressiveness of the prostate cancer.

Also provided by this invention is a method for identifying metastatic prostate cancer in a subject, comprising assessing the level of Pin1 in a biological sample from the subject, wherein an elevation in the level of Pin1 is indicative of metastatic prostate cancer.

The invention further provides a method for identifying a subject at risk for developing metastatic prostate cancer comprising assessing the level of Pin1 in a biological sample from the subject, wherein an elevation in the level of Pin1 is indicative of that the subject is at risk for developing metastatic prostate cancer.

Further, provided by this invention are the above methods, where assessing the level of Pin1 in a biological sample from the subject includes contacting the biological sample with an antibody to Pin1 or a fragment thereof; determining the amount of binding of the antibody to the biological sample; and comparing the amount of antibody bound to the biological sample to a predetermined base level. The amount of binding of the antibody to the biological sample can be determined by the intensity of the signal emitted by the labeled antibody and/or by the number cells in the biological sample bound to the labeled antibody.

Also encompassed by this invention are the above methods wherein the level of Pin1 is assessed by detecting a level of Pin1 nucleic acid in a biological sample; and comparing the level of Pin1 in the biological sample with a level of Pin1 in a control sample. For example, in certain embodiments Pin1 nucleic acid is detected using hybridization probes and/or nucleic acid amplification methods The diagnostic and prognostic assays of this invention can be used in combination with other methods of prostate cancer diagnosis. Examples of prostate diagnostic methods that can be used in combination with the assays of the invention include, but are not limited to, current diagnostic methods for PCA known to medical practitioners skilled in the art such as the PSA test, rectal examination, transrectal ultrasonography or magnetic resonance imaging (MRI), bone scanning, X-rays, skeletal survey, intravenous pyelography, CAT-scan, and biopsy. In an embodiment, the subject in the above diagnostic and prognostic assays of this invention was identified by a digital rectal exam as having a prostate abnormality. In another embodiment, the subject was identified as having elevated PSA levels. In other embodiments, markers for prostate cancer which can be used in combination with the methods of the invention include prostatic acid phosphatase, prostate secreted protein, prostate specific membrane antigen, human kallekrein 2, prostate specific transglutaminase, keratin-19, and interleukin 8.

The diagnostic and prognostic assays of this invention are particularly useful when the PSA level falls within a gray zone where it is not clear whether a prostate biopsy should be performed. For example, the diagnostic and prognostic assays of this invention may be used when the subject has a blood serum concentration of the prostate-specific antigen of between about 4 and about 8 ng/ml. The prognostic assays of this invention are also particularly useful when the Gleason sum falls within a gray zone where the prognosis is usually unclear, for example a Gleason score between 4 and 8, or a Gleason score of 6 to 7.

The diagnostic and prognostic assays of this invention can also be used in combination with other methods of prostate cancer staging. The assays of this invention are particularly useful when conventional staging methods leave unclear the prognosis of the prostate cancer. For example, the aggressiveness of a T2 or T3 stage prostate cancer can be better assessed using the assays of this invention.

The present invention also includes methods of determining whether a subject is likely to respond to a treatment regimen comprising agents, or modulators which have a stimulatory or inhibitory effect on Pin1 activity (e.g., Pin1 gene expression or enzyme activity). For example, Pin1 inhibitors can be administered to individuals, such as those identified using the diagnostic and prognostic methods of the invention as having elevated levels of Pin1, to treat (prophylactically or therapeutically) disorders (e.g, proliferative disorders such as cancer) associated with aberrant Pin1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether use of a Pin1 inhibitor would be efficatious. Information generated from pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a Pin1 molecule or Pin1 modulator, such as a modulator identified by one of the exemplary screening assays described herein. Thus, the methods described herein can be used to determine which Pin1 modulator or inhibitor to administer and whether to administer a Pin1 molecule or Pin1 modulator as well as tailoring the dosage and/or therapeutic regimen of treatment with a Pin1 molecule or Pin1 modulator.

The diagnostic and prognostic assays of this invention are also useful in assessing the recovery of a subject who is receiving, or has received, therapy for a state associated with prostate cancer. For example, the assays of this invention can be used alone or in combination with PSA failure to assess recovery after prostate treatment (i.e. prostate removal surgery).

The invention also encompasses kits for detecting the presence of a Pin1 polypeptide or nucleic acid in a biological sample according to the methods described herein. Such kits can be used to determine if a subject is suffering from or is at increased risk of developing prostate cancer, and for identifying subjects who have, or are at risk of developing metastatic prostate cancer. For example, the kit can comprise a labeled compound or agent capable of detecting Pin1 or an mRNA encoding a Pin1 in a biological sample and means for determining the amount of the Pin1 or Pin1 mRNA in the sample (e.g., an antibody which binds the polypeptide or an oligonucleotide probe which binds to DNA or mRNA encoding Pin1). Kits can also include immunomagnetic beads that can be used to facilitate serum assays. Kits can also include instructions for carrying out the methods of the invention and/or for interpreting the results obtained from using the kit.

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the biological sample. Each component of the kit can be enclosed within an individual container and all of the various containers can be within a single package, along with instructions for interpreting the results of the assays performed using the kit.

In certain embodiments kit for diagnosing prostate cancer includes: at least one reagent for assaying levels of Pin1 in a sample from a subject, and instructions for using the at least one reagent to diagnose prostate cancer based on assay levels of Pin1 in a sample from a subject. An example of a kit for assessing the aggressiveness of prostate cancer in a subject includes: at least one reagent for assaying levels of Pin1 in a sample from a subject, and instructions for using the at least one reagent to assess the aggressiveness prostate cancer based on assay levels of Pin1 in a sample from a subject.

DETAILED DESCRIPTION OF THE INVENTION

Figure 1:
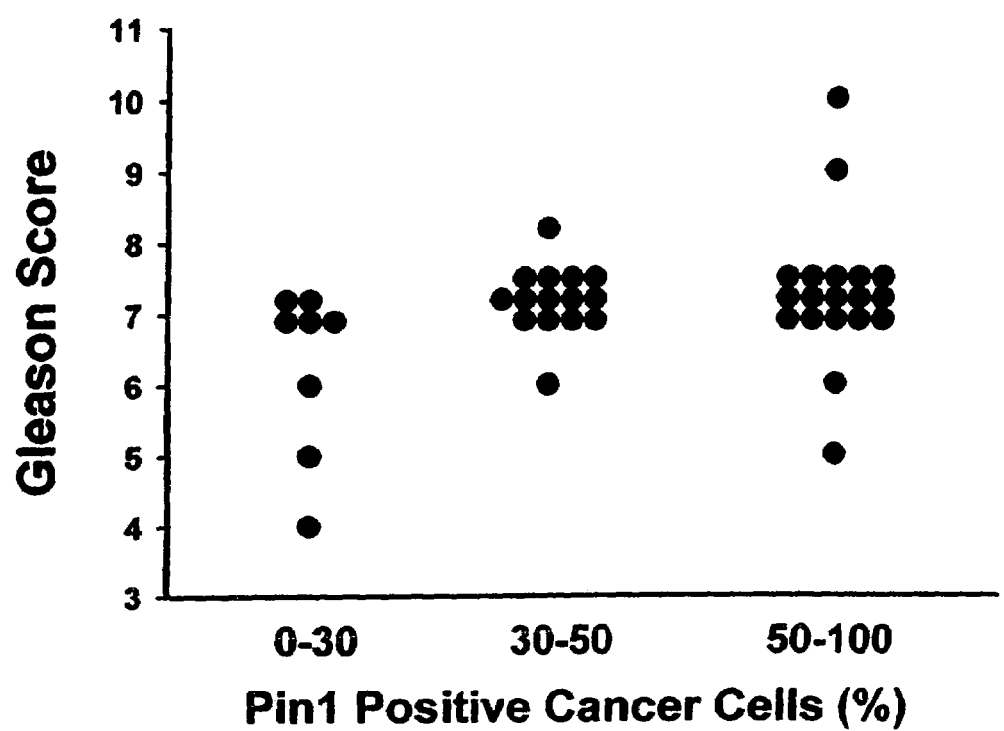
FIG. 1 shows the correlation between Pin1 expression and Gleason sum based on 42 specimens of human prostate carcinomas with Gleason scores of 4-10. Each symbol represents a specimen from a different individual.

This invention provides methods for diagnosing prostate cancer, methods for measuring the aggressiveness of prostate cancer, and methods for identifying prostate cancer likely to metastasize. The diagnostic and prognostic assays of this invention include methods involving the antibody-based detection of Pin1 and the amplification of Pin1 RNA. The diagnostic and prognostic assays of this invention may be used in combination with other methods of prostate cancer diagnosis including the PSA test, digital rectal exam, and Gleason prostate tumor grading system. The methods are an improvement over currently available methods due to the precise nature of the measurement and the ability to use these methods without invasive surgery.

Definitions

"Pin 1" is a highly conserved protein that binds and regulates the function of a defined subset of proteins that have been phosphorylated by Pro-directed kinases. Yaffe, et al. 1997. Science 278:1957-1960. Shen, et al. 1998. Genes Dev. 12:706-720. Lu, et al. 1999. Science 283:1325-1328. Crenshaw, et al. 1998. Embo J. 17:1315-1327. Lu, et al. 1999. Nature 399:784-788. Zhou, et al. 1999 Cell Mol. Life Sci. 56:788-806.

Human Pin1 has the following amino acid sequence:

```
                                      (SEQ ID NO:1)
    MADEEKLPPG WEKRMSRSSG RVYYFNHITN ASQWERPSGN

SSSGGKNGQG EPARVRCSHL LVKHSQSRRP SSWRQEKITR

TKEEALELIN GYIQKIKSGE EDFESLASQF SDCSSAKARG
```

```
                                      -continued
    DLGAFSRGQM QKPFEDASFA LRTGEMSGPV FTDSGIHIIL

RTE.
```

Pin1 contains an $NH_2$-terminal WW domain and a COOH-terminal peptidyl-prolyl isomerase (PPIase) domain. The WW domain binds specific pS/T-P motifs and targets Pin1 to its phosphoprotein substrates, where the PPIase domain regulates their conformations and functions, presumably by isomerizing specific pS/T-P bonds.

"Cancer" includes a malignant neoplasm characterized by deregulated or uncontrolled cell growth. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

"Anaplasia" refers to the histological features of cancer. These features include derangement of the normal tissue architecture, the crowding of cells, lack of cellular orientation termed dyspolarity, cellular heterogeneity in size and shape termed "pleomorphism." The cytologic features of anaplasia include an increased nuclear-cytoplasmic ratio (the nuclear-cytoplasmic ratio can be over 50% for malignant cells), nuclear pleomorphism, clumping of the nuclear chromatin along the nuclear membrane, increased staining of the nuclear chromatin, simplified endoplasmic reticulum, increased free ribosomes, pleomorphism of mitochondria, decrease in size and number of organelles, enlarged and increased numbers of nucleoli, and sometimes the presence of intermediate filaments.

"Neoplasia" or "neoplastic transformation" is the pathologic process that results in the formation and growth of a neoplasm, tissue mass, or tumor. Such process includes uncontrolled cell growth, including either benign or malignant tumors. Neoplasms include abnormal masses of tissue, the growth of which exceeds and is uncoordinated with that of the normal tissues and persists in the same excessive manner after cessation of the stimuli which evoked the change. Neoplasms may show a partial or complete lack of structural organization and functional coordination with the normal tissue, and usually form a distinct mass of tissue.

Neoplasms tend to morphologically and functionally resemble the tissue from which they originated. For example, neoplasms arising within the islet tissue of the pancreas resemble the islet tissue, contain secretory granules, and secrete insulin. Clinical features of a neoplasm may result from the function of the tissue from which it originated.

By assessing the histologic and other features of a neoplasm, it can be determined whether the neoplasm is benign or malignant. Invasion and metastasis (the spread of the neoplasm to distant sites) are definitive attributes of malignancy. Despite the fact that benign neoplasms may attain enormous size, they remain discrete and distinct from the adjacent non-neoplastic tissue. Benign tumors are generally well circumscribed and round, have a capsule, and have a grey or white color, and a uniform texture. By contrast, malignant tumor generally have fingerlike projections, irregular margins, are not circumscribed, and have a variable color and texture. Benign tumors grow by pushing on adjacent tissue as they grow. As the benign tumor enlarges it compresses adjacent tissue, sometimes causing atrophy. The junction between a benign tumor and surrounding tissue may be converted to a fibrous connective tissue capsule allowing for easy surgical remove of benign tumors. By contrast, malignant tumors are locally invasive and grow into the adjacent tissues usually giving rise to irregular margins that are not encapsulated making it necessary to remove a wide margin of normal tissue for the surgical removal of malignant tumors. Benign neoplasms tends to grow more slowly than malignant tumors. Benign neoplasms also tend to be less autonomous than malignant tumors. Benign neoplasms tend to closely histologically resemble the tissue from which they originated. More high differentiated cancers, cancers that resemble the tissue from which they originated, tend to have a better prognosis than poorly differentiated cancers. Malignant tumors are more likely than benign tumors to have an aberrant function (i.e. the secretion of abnormal or excessive quantities of hormones).

"Prostate cancer" is an adenocarcinoma of the prostate gland. The prostate gland is a walnut sized organ that helps the body form semen. The prostate gland is located where the urethra joins the neck of the urinary bladder. The term "prostate cancer" (PCA) as used herein refers to both the appearance of a palpable tumor of the prostate, and also to microscopically detectable neoplastic or transformed cells in the prostate gland. In the latter case, the said cytologically-detectable prostate cancer may be asymptomatic, in that neither the patient nor the medical practitioner detects the presence of the cancer cells. Prostate cancer usually progresses gradually and usually expands to adjacent tissue and lymph glands before detection. In the event that prostate cancer metastasizes to additional sites distal to the prostate, the condition is described as metastatic cancer (MC), or prostate cancer, metastasized, to distinguish this condition from organ-confined prostate cancer. PCA fatality results from metastatic dissemination of prostatic adenocarcinoma cells to distant sites, usually in the axial skeleton. As the disease progresses, other organs including the bones, lungs, and liver can become cancerous.

"Benign prostatic hypertrophy," comprises an age-related non-cancerous enlargement of the prostate, and affects more than 50% of men over age 45. Benign prostatic hypertrophy (BPH) may be asymptomatic, that is, have no negative consequences for the individual, and is not intended here to imply the necessary development of prostate cancer. BPH is accompanied by an increase in production of the protein prostate specific antigen, proportional to the extent of growth of the prostate gland. For this reason, the diagnosis of PCA in a BPH patient may be difficult to distinguish from further asymptomatic growth by sole use of the PSA test.

BPH may appear as or may progress to "problematic" prostatic hyperplasia, with symptoms that include urinary urgency, frequency, and hesitancy, and penile erectile difficulties. Since these same symptoms are associated with PCA (M. Garnick, (1993), *Annals Int. Med.,* 118(10):804-818), the clinician distinguishes PCA and problematic prostatic hyperplasia by the suddenness in onset of symptoms, and by additional diagnostic tests. BPH and problematic prostatic hypertrophy may also progress to PCA, however these terms are meant neither to exclude nor to imply disease progression, as the full range of diagnostic possibilities is found for the BPH patient population as for the normal subject.

"Invasive" or "aggressive" as used herein with respect to cancer refers to the proclivity of a tumor for expanding beyond its boundaries into adjacent tissue, or to the characteristic of the tumor with respect to metastasis (Darnell, J. (1990), *Molecular Cell Biology*, Third Ed., W. H. Freeman, NY). Invasive cancer can be contrasted with organ-confined cancer. For example, a basal cell carcinoma of the skin is a non-invasive or minimally invasive tumor, confined to the site of the primary tumor and expanding in size, but not metastasizing. In contrast, the cancer melanoma is highly invasive of adjacent and distal tissues. The invasive property of a tumor is often accompanied by the elaboration of proteolytic enzymes, such as collagenases, that degrade matrix material and basement membrane material to enable the tumor to expand beyond the confines of the capsule, and beyond confines of the particular tissue in which that tumor is located.

"Organ-confined" as used herein with respect to prostate cancer refers to prostate cancer that has not metastasized beyond the boundaries of the prostate gland, i.e., has not been found by techniques familiar to those skilled in the art to occur in any organs or tissues beyond the prostate gland. It can not be ruled out, however, that some number of cells have metastasized, however they are not detected by ordinary techniques used by those with skill in the art.

The term "metastasis" as used herein refers to the condition of spread of cancer from the organ of origin to additional distal sites in the patient. The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Increased malignant cell motility has been associated with enhanced metastatic potential in animal as well as human tumors (Hosaka, et al., Gann 69, 273-276 (1978) and Haemmerlin, et al., Int. J. Cancer 27, 603-610 (1981)).

"Metastatic prostate cancer" includes prostate cancers which have spread to regional lymph nodes or to distant sites. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

"Subject" includes living organisms, e.g., prokaryotes and eukaryotes. Examples of subjects include mammals, e.g., humans, dogs, cows, horses, kangaroos, pigs, sheep, goats, cats, mice, rabbits, rats, and transgenic non-human animals. Most preferably the subject is a human.

"TDPCA" is a test done to facilitate diagnosis of prostate cancer. For example, TDPCA includes a test for the detection of a prostate cancer marker is selected from the group consisting of: prostatic acid phosphatase, prostate secreted protein, prostate specific membrane antigen, human kallekrein 2, prostate specific transglutaminase, and interleukin 8. Examples of TDPCA include the PSA test, rectal examination, transrectal ultrasonography or magnetic resonance imaging (MRI), bone scanning, X-rays, skeletal survey, intravenous pyelography, CAT-scan, and biopsy. In an embodiment, TDPCA is a digital rectal exam. In a preferred embodiment, TDPCA is a test for the detection of prostate-specific antigen in the blood serum of the subject. TDPCA does not include a test to detect Pin1.

"Biological samples" include solid and body fluid samples. The biological samples of the present invention may include cells, protein or membrane extracts of cells, blood or biological fluids such as ascites fluid or brain fluid (e.g., cerebrospinal fluid). Examples of solid biological samples include samples taken from feces, the rectum, central nervous system, bone, breast tissue, renal tissue, the uterine cervix, the endometrium, the head/neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, and the thymus. Examples of "body fluid samples" include samples taken from the blood, serum, semen, prostate fluid, seminal fluid, urine, saliva, sputum, mucus, bone marrow, lymph, and tears. For amplifying Pin1 RNA, the preferred samples include peripheral venous blood samples and prostate tissue samples. Samples for use in the assays of the invention can be obtained by standard methods including venous puncture and surgical biopsy. In one embodiment, the biological sample is a prostate tissue sample obtained by needle biopsy.

"Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment according to that individual's drug response genotype.

Diagnostic and Prognostic Methods

As described in more detail below, the detection methods of the invention can be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations, immunohistochemistry and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques. Nucleic acid probes as well as antibodies to Pin1 for use in these methods can readily be designed since the nucleic and amino acid sequence of Pin1 is known (Hunter et al., WO 97/17986 (1997); Hunter et al., U.S. Pat. Nos. 5,952,467 and 5,972,697).

I. Antibody-Based Assays

In embodiments of the above methods, assessing the level of Pin1 in a biological sample from the subject includes contacting the biological sample with an antibody to Pin 1 or a fragment thereof; determining the amount of binding of the antibody to the biological sample; and comparing the amount of antibody bound to the biological sample to a predetermined base level.

The level of Pin-1 in normal (i.e. non-cancerous) biological samples can be assessed in a variety of ways. In one embodiment, this normal level of expression is determined by assessing the level of Pin-1 in a portion of prostate cells which appears to be non-cancerous and by comparing this normal level with the level of Pin-1 in a portion of the prostate cells which is suspected of being cancerous. Alternatively, the 'normal' level of expression of a marker may be determined by assessing the level of Pin-1 in a sample or samples obtained from a non-cancer-afflicted individuals.

"Antibody" includes immunoglobulin molecules and immunologically active determinants of immunoglobulin molecules, i.e., molecules that contain an antigen binding site which specifically binds (immunoreacts with) an antigen. Structurally, the simplest naturally occurring antibody (e.g., IgG) comprises four polypeptide chains, two copies of a heavy (H) chain and two of a light (L) chain, all covalently linked by disulfide bonds. Specificity of binding in the large and diverse set of antibodies is found in the variable (V) determinant of the H and L chains; regions of the molecules that are primarily structural are constant (C) in this set. Antibody includes polyclonal antibodies, monoclonal antibodies, whole immunoglobulins, and antigen binding fragments of the immunoglobulins.

The binding sites of the proteins that comprise an antibody, i.e., the antigen-binding functions of the antibody, are localized by analysis of fragments of a naturally-occurring antibody. Thus, antigen-binding fragments are also intended to be designated by the term "antibody." Examples of binding fragments encompassed within the term antibody include: a Fab fragment consisting of the $V_L$, $V_H$, $C_L$ and $C_{H1}$ domains; an $F_d$ fragment consisting of the $V_H$ and $C_{H1}$ domains; an $F_v$ fragment consisting of the $V_L$ and $V_H$ domains of a single arm of an antibody; a dAb fragment (Ward et al., 1989 Nature 341: 544-546) consisting of a $V_H$ domain; an isolated complementarily determining region (CDR); and an F(ab')$_2$ fragment, a bivalent fragment comprising two Fab' fragments linked by a disulfide bridge at the hinge region. These antibody fragments are obtained using conventional techniques well-known to those with skill in the art, and the fragments are screened for utility in the same manner as are intact antibodies. The term "antibody" is further intended to include bispecific and chimeric molecules having at least one antigen binding determinant derived from an antibody molecule.

In the diagnostic and prognostic assays of the invention, the antibody can be a polyclonal antibody or a monoclonal antibody and in a preferred embodiment is a labeled antibody.

Polyclonal antibodies are produced by immunizing animals, usually a mammal, by multiple subcutaneous or intraperitoneal injections of an immunogen (antigen) and an adjuvant as appropriate. As an illustrative embodiment, animals are typically immunized against a protein, peptide or derivative by combining about 1 µg to 1 mg of protein capable of eliciting an immune response, along with an enhancing carrier preparation, such as Freund's complete adjuvant, or an aggregating agent such as alum, and injecting the composition intradermally at multiple sites. Animals are later boosted with at least one subsequent administration of a lower amount, as ⅕ to 1⁄10 the original amount of immunogen in Freund's complete adjuvant (or other suitable adjuvant) by subcutaneous injection at multiple sites. Animals are subsequently bled, serum assayed to determine the specific antibody titer, and the animals are again boosted and assayed until the titer of antibody no longer increases (i.e., plateaus).

Such populations of antibody molecules are referred to as "polyclonal" because the population comprises a large set of antibodies each of which is specific for one of the many differing epitopes found in the immunogen, and each of which is characterized by a specific affinity for that epitope. An epitope is the smallest determinant of antigenicity, which for a protein, comprises a peptide of six to eight residues in length (Berzofsky, J. and I. Berkower, (1993) in Paul, W., Ed., *Fundamental Immunology*, Raven Press, N.Y., p. 246). Affinities range from low, e.g. $10^{-6}$ M, to high, e.g., $10^{-11}$ M.

The polyclonal antibody fraction collected from mammalian serum is isolated by well known techniques, e.g. by chromatography with an affinity matrix that selectively binds immunoglobulin molecules such as protein A, to obtain the IgG fraction. To enhance the purity and specificity of the antibody, the specific antibodies may be further purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. Bound antibodies are eluted from the solid phase by standard techniques, such as by use of buffers of decreasing pH or increasing ionic strength, the eluted fractions are assayed, and those containing the specific antibodies are combined.

"Monoclonal antibody" or "monoclonal antibody composition" as used herein refers to a preparation of antibody molecules of single molecular composition. A monoclonal antibody composition displays a single binding specificity and affinity for a particular epitope. Monoclonal antibodies can be prepared using a technique which provides for the production of antibody molecules by continuous growth of cells in culture. These include but are not limited to the hybridoma technique originally described by Kohler and Milstein (1975, *Nature* 256:495-497; see also Brown et al. 1981 *J. Immunol* 127:539-46; Brown et al., 1980, *J Biol Chem* 255:4980-83; Yeh et al., 1976, *PNAS* 76:2927-31; and Yeh et al., 1982, *Int. J. Cancer* 29:269-75) and the more recent human B cell hybridoma technique (Kozbor et al., 1983, *Immunol Today* 4:72), EBV-hybridoma technique (Cole et al., 1985, Monoclonal Antibodies and Cancer Therapy, Alan R. Liss, Inc., pp. 77-96), and trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

A monoclonal antibody can be produced by the following steps. In all procedures, an animal is immunized with an antigen such as a protein (or peptide thereof) as described above for preparation of a polyclonal antibody. The immunization is typically accomplished by administering the immunogen to an immunologically competent mammal in an immunologically effective amount, i.e., an amount sufficient to produce an immune response. Preferably, the mammal is a rodent such as a rabbit, rat or mouse. The mammal is then maintained on a booster schedule for a time period sufficient for the mammal to generate high affinity antibody molecules as described. A suspension of antibody-producing cells is removed from each immunized mammal secreting the desired antibody. After a sufficient time to generate high affinity antibodies, the animal (e.g., mouse) is sacrificed and antibody-producing lymphocytes are obtained from one or more of the lymph nodes, spleens and peripheral blood. Spleen cells are preferred, and can be mechanically separated into individual cells in a physiological medium using methods well known to one of skill in the art. The antibody-producing cells are immortalized by fusion to cells of a mouse myeloma line. Mouse lymphocytes give a high percentage of stable fusions with mouse homologous myelomas, however rat, rabbit and frog somatic cells can also be used. Spleen cells of the desired antibody-producing animals are immortalized by fusing with myeloma cells, generally in the presence of a fusing agent such as polyethylene glycol. Any of a number of myeloma cell lines suitable as a fusion partner are used with to standard techniques, for example, the P3-NS1/1-Ag4-1, P3-x63-Ag8.653 or Sp2/O-Ag14 myeloma lines, available from the American Type Culture Collection (ATCC), Rockville, Md.

The fusion-product cells, which include the desired hybridomas, are cultured in selective medium such as HAT medium, designed to eliminate unfused parental myeloma or lymphocyte or spleen cells. Hybridoma cells are selected and are grown under limiting dilution conditions to obtain isolated clones. The supernatants of each clonal hybridoma is screened for production of antibody of desired specificity and affinity, e.g., by immunoassay techniques to determine the desired antigen such as that used for immunization. Monoclonal antibody is isolated from cultures of producing cells by conventional methods, such as ammonium sulfate precipitation, ion exchange chromatography, and affinity chromatography (Zola et al., Monoclonal Hybridoma Antibodies: Techniques And Applications, Hurell (ed.), pp. 51-52, CRC Press, 1982). Hybridomas produced according to these methods can be propagated in culture in vitro or in vivo (in ascites fluid) using techniques well known to those with skill in the art.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening an antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

"Labeled antibody" as used herein includes antibodies that are labeled by a detectable means and includes enzymatically, radioactively, fluorescently, chemiluminescently, and/or bioluminescently labeled antibodies.

One of the ways in which an antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the Pin 1-specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection may be accomplished using any of a variety of immunoassays. For example, by radioactively labeling an antibody, it is possible to detect the antibody through the use of radioimmune assays. A description of a radioimmune assay (RIA) may be found in Laboratory Techniques and Biochemistry in Molecular Biology, by Work, T. S., et al., North Holland Publishing Company, NY (1978), with particular reference to the chapter entitled "An Introduction to Radioimmune Assay and Related Techniques" by Chard, T.

The radioactive isotope can be detected by such means as the use of a gamma counter or a scintillation counter or by audioradiography. Isotopes which are particularly useful for the purpose of the present invention are: $^{3}H$, $^{131}I$, $^{35}S$, $^{14}C$, and preferably $^{125}I$.

It is also possible to label an antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}Eu$, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

Likewise, a bioluminescent compound may be used to label an antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In the diagnostic and prognostic assays of the invention, the amount of binding of the antibody to the biological sample can be determined by the intensity of the signal emitted by the labeled antibody and/or by the number cells in the biological sample bound to the labeled antibody.

Serum Assays

A serum assay for detecting a cancer marker is a non-evasive method, which is more acceptable to patients and also provides a tool for screening large number of samples. Additional advantages include that the antibody recognizes an antigen that is related to the early events rather than the later stages of progression to the metastatic phenotype. Serum assays can be used in conjunction with other assays presented herein to diagnose cancer.

Antibodies directed toward a protein of interest can be connected to magnetic beads and used to enrich a population. Immunomagnetic selection has been used previously for this purpose and examples of this method can be found, for example, at U.S. Pat. No. 5,646,001; Ree et al. (2002) *Int. J. Cancer* 97:28-33; Molnar et al. (2001) *Clin. Cancer Research* 7:4080-4085; and Kasimir-Bauer et al. (2001) *Breast Cancer Res. Treat.* 69:123-32. An antibody, either polyclonal or monoclonal, that is specific for a cell surface protein on a cell of interest is attached to a magnetic substrate thereby allowing selection of only those cells that express the surface protein of interest. Once a population of cells is selected, the following assays can be performed to test for the presence of Pin1.

Immunoassays

The amount of an antigen (i.e. Pin1) in a biological sample may be determined by a radioimmunoassay, an immunoradiometric assay, and/or an enzyme immunoassay.

"Radioimmunoassay" is a technique for detecting and measuring the concentration of an antigen using a labeled (i.e. radioactively labeled) form of the antigen. Examples of radioactive labels for antigens include $^{3}H$, $^{14}C$, and $^{125}I$. The concentration of antigen (i.e. Pin1) in a sample (i.e. biological sample) is measured by having the antigen in the sample compete with a labeled (i.e. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (i.e. covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

A "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." The "Enzyme-Linked Immunosorbent Assay (ELISA)" is a technique for detecting and measuring the concentration of an antigen using a labeled (i.e. enzyme linked) form of the antibody.

In a "sandwich ELISA", an antibody (i.e. to Pin1) is linked to a solid phase (i.e. a microtiter plate) and exposed to a biological sample containing antigen (i.e. Pin1). The solid phase is then washed to remove unbound antigen. A labeled (i.e. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and β-galactosidase. The enzyme linked antibody reacts with a substrate to generate a colored reaction product that can be assayed for.

In a "competitive ELISA", antibody is incubated with a sample containing antigen (i.e. Pin1). The antigen-antibody mixture is then contacted with an antigen-coated solid phase (i.e. a microtiter plate). The more antigen present in the sample, the less free antibody that will be available to bind to the solid phase. A labeled (i.e. enzyme linked) secondary antibody is then added to the solid phase to determine the amount of primary antibody bound to the solid phase.

In a "immunohistochemistry assay" a section of tissue for is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or β-galactosidase), or chemical methods (e.g., DAB/ Substrate chromagen).

II. Pin1 Nucleic Acid-Based Diagnostic and Prognostic Methods

Also encompassed by this invention is a method of diagnosing prostate cancer in a subject, comprising: detecting a level of Pin1 nucleic acid in a biological sample; and comparing the level of Pin1 in the biological sample with a level of Pin1 in a control sample, wherein an elevation in the level of Pin1 in the biological sample compared to the control sample is indicative of prostate cancer.

In addition, this invention pertains to a method of diagnosing prostate cancer metastasis in a subject, comprising the steps of: detecting a level of Pin1 nucleic acid in a biological sample; and comparing the level of Pin1 in the biological sample with a level of Pin1 in a control sample, wherein an elevation in the level of Pin1 in the biological sample compared to the control sample is indicative of prostate cancer metastasis.

In an embodiment of the above methods, the detecting a level of Pin1 nucleic acid in a biological sample includes amplifying Pin1 RNA. In another embodiment of the above methods, the detecting a level of Pin1 nucleic acid in a biological sample includes hybridizing the Pin1 RNA with a probe.

As an alternative to making determinations based on the absolute expression level of the Pin1 marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-prostate cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the biological sample (absolute level of expression) is then divided by the mean expression value obtained for that marker. This provides a relative expression level.

One preferred diagnostic method for the detection of mRNA levels involves contacting the isolated mRNA with a nucleic acid molecule (probe) that can hybridize to the mRNA encoded by the gene being detected. Probes based on the sequence of a nucleic acid molecule of the invention can be used to detect transcripts corresponding to Pin-1. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Hybridization of an mRNA with the probe indicates that the marker in question is being expressed. In an embodiment, the probe includes a label group attached thereto, e.g., a radioisotope, a fluorescent compound, an enzyme, or an enzyme co-factor.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

"Amplifying" refers to template-dependent processes and vector-mediated propagation which result in an increase in the concentration of a specific nucleic acid molecule relative to its initial concentration, or in an increase in the concentration of a detectable signal. As used herein, the term template-dependent process is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, J. D. et al., In: Molecular Biology of the Gene, 4th Ed., W. A. Benjamin, Inc., Menlo Park, Calif. (1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., Molecular Cloning (A Laboratory Manual), Cold Spring Harbor Laboratory, 1982.

A number of template dependent processes are available to amplify the target sequences of interest present in a sample. One of the best known amplification methods is the polymerase chain reaction (PCR) which is described in detail in Mullis, et al., U.S. Pat. No. 4,683,195, Mullis, et al., U.S. Pat. No. 4,683,202, and Mullis, et al., U.S. Pat. No. 4,800,159, and in Innis et al., PCR Protocols, Academic Press, Inc., San Diego Calif., 1990. Briefly, in PCR, two primer sequences are prepared which are complementary to regions on opposite complementary strands of the target sequence.

An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of mRNA amplified. Polymerase chain reaction methodologies are well known in the art.

Another method for amplification is the ligase chain reaction (LCR), disclosed in European Patent No. 320,308B1. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. Whiteley, et al., U.S. Pat. No. 4,883,750 describes an alternative method of amplification similar to LCR for binding probe pairs to a target sequence.

Qbeta Replicase, described in PCT Application No. PCT/US87/00880 may also be used as still another amplification method in the present invention. In this method, a replicative sequence of RNA which has a region complementary to that of a target is added to a sample in the presence of an RNA polymerase. The polymerase will copy the replicative sequence which can then be detected.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Prostate specific sequences can also be detected using a cyclic probe reaction (CPR). In CPR, a probe having a 3' and 5' sequences of non-prostate specific DNA and middle sequence of prostate specific RNA is hybridized to DNA which is present in a sample. Upon hybridization, the reaction is treated with Rnase H, and the products of the probe identified as distinctive products generating a signal which are released after digestion. The original template is annealed to another cycling probe and the reaction is repeated. Thus, CPR involves amplifying a signal generated by hybridization of a probe to a prostate cancer specific expressed nucleic acid.

Still other amplification methods described in GB Application No. 2 202 328, and in PCT Application No. PCT/US89/01025 may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh D., et al., Proc. Natl. Acad. Sci. (U.S.A.) 1989, 86:1173, Gingeras T. R., et al., PCT Application WO 88/1D315), including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has prostate specific sequences. Following polymerization, DNA/RNA hybrids are digested with RNase H while double stranded DNA molecules are heat denatured again. In either case the single stranded DNA is made fully double stranded by addition of second prostate specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate prostate cancer specific sequences.

Davey, C., et al., European Patent No. 329,822B1 disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT Application WO 89/06700 discloses a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., In: PCR Protocols: A Guide to Methods and Applications 1990, Academic Press, New York) and "one-sided PCR" (Ohara, O., et al., Proc. Natl. Acad. Sci. (U.S.A.) 1989, 86:5673-5677).

Methods based on ligation of two (or more) oligonucleotides in the presence of nucleic acid having the sequence of the resulting "di-oligonucleotide", thereby amplifying the di-oligonucleotide (Wu, D. Y. et al., Genomics 1989, 4:560), may also be used in the amplification step of the present invention.

Following amplification, the presence or absence of the amplification product may be detected. The amplified product may be sequenced by any method known in the art, including and not limited to the Maxam and Gilbert method. The sequenced amplified product is then compared to a sequence known to be in a prostate cancer specific sequence. Alternatively, the nucleic acids may be fragmented into varying sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labeled probe is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 200 nucleotides in length. Various labels for visualization or detection are known to those of skill in the art, such as and not limited to fluorescent staining, ethidium bromide staining for example, avidin/biotin, radioactive labeling such as $^{32}P$ labeling, and the like. Preferably, the product, such as the PCR product, may be run on an agarose gel and visualized using a stain such as ethidium bromide. The matrix may then be analyzed by autoradiography to locate particular fragments which hybridize to the probe.

III. Assays for Use in Combination with Pin1 Detection

A. PSA Assays

The level of "prostate-specific antigen" (PSA) in the blood is currently the primary diagnostic tool for disorders of the prostate. The presence of Prostate Specific Antigen (PSA) can be measured with relative ease from blood samples using standard antibody-based detection kits. Prostate enlargement, a condition known as benign prostatic hyperplasia (BPH), is found in about half of men over age 45. With BPH, PSA levels rise in proportion to prostate size, possibly obscuring diagnosis of PCA. In addition, a significant proportion of men with PCA have normal PSA levels. The PSA test is somewhat non-specific for distinguishing PCA and BPH, and produces a degree of false negative results (Garnick, M., (1993), *Am. Inst. Med.,* 118:804-818). In the majority of cases, PSA elevation is due to BPH or prostatitis rather than carcinoma. The normal level of prostate-specific antigen (PSA) in blood increases with age and ranges from 0-2.5 ng/ml for men 40 to 49 years old to 0-6.5 ng/ml for men 70-79 years old. (See Table 1, which follows, for variation of normal PSA levels with age. Prostate cancer will be detected in approximately one-third of men with PSA levels between 4.1 and 10 ng/ml. Approximately two-thirds of men with PSA levels above 10 ng/ml have prostate cancer. Approximately 20% of men with prostate cancer have PSA levels below 4 ng/ml.

TABLE 1

Age-Specific Prostate-Specific Antigen (PSA) Values
Normal PSA values (ng/ml)*

| Age range (yr) | Mayo Clinic White | Walter Reed White | Black |
|---|---|---|---|
| 40-49 | 0-2.5 | 0-2.5 | 0.2.0 |
| 50-59 | 0-3.5 | 0-3.5 | 0-4.0 |
| 60-69 | 0-4.5 | 0-3.5 | 0-4.5 |
| 70-79 | 0-6.5 | 0-3.5 | 0-5.5 |

In addition to the serum PSA concentration, the percent-free PSA and PSA velocity can also be used to help diagnose prostate cancer.

PSA exists in 2 forms in the blood: protein bound and free. Examples of bound PSA are PSA bound with α1-antichymotrypsin (PSA-ACT) or α2-macroglobulin. In BPH, there is generally a higher percentage free (as opposed to bound) PSA than in prostate cancer. For example, a percent-free PSA between 0 and 14% with a PSA level between about 4.1 and 10 ng/ml is associated with a 64% chance of a biopsy positive for prostate cancer. In another example, a percent-free PSA between 15 and 24% with a PSA level between about 4.1 and 10 ng/ml is associated with a 37% chance of a biopsy positive for prostate cancer. See Table 2, which follows, shows the probability of a positive prostate biopsy based on the percent-free PSA.

TABLE 2

Probability of Positive Prostate Biopsy Based on
Percent-Free Prostate-Specific Antigen (PSA)

| Percent-Free PSA | Estimated probability of positive biopsy |
|---|---|
| Patients with PSA in 4.1-10 ng/mL range: | |
| 0%-14% | 64% |
| 15-24% | 37% |
| >24% | 10% |
| Patients with PSA in 2.6-4 ng/mL range: | |
| 0%-14% | 25% |
| 15%-24% | 23% |
| >24% | 18% |

"PSA velocity" is the rate of change in PSA concentration. Because prostate cancer may raise the PSA level more quickly than BPH, a higher PSA velocity correlates with an increased likelihood of prostate cancer. For example, a PSA velocity of greater than 0.75 ng/ml per year may indicate prostate cancer even with a PSA of less than 4 ng/ml.

The diagnostic and prognostic assays of this invention are particularly useful when the PSA level falls within a gray zone where it is not clear whether a prostate biopsy should be performed. For example, the diagnostic and prognostic assays of this invention may be used to detect prostate cancer and assess the subject's prospects when: (a) the subject has a blood serum concentration of the prostate-specific antigen of between about 2 and about 10 ng/ml; (b) the subject has a blood serum concentration of the prostate-specific antigen of between about 4 and about 8 ng/ml; (c) the subject has a blood serum concentration of the prostate-specific antigen of between about 3 and about 7 ng/ml and is between about 40 and about 60 years old; (d) the subject has a blood serum concentration of the prostate-specific antigen of between about 5 and about 9 ng/ml and is between about 60 and about 80 years old; (e) the subject has a blood serum concentration of the prostate-specific antigen of less than about 4 ng/ml and a PSA velocity of greater than about 0.7 ng/ml per year; and (f) the subject has a blood serum concentration of the prostate-specific antigen of between about 4 and about 8 ng/ml and a percent-free prostate-specific antigen of between about 15 and about 25%.

B. Methods of Staging Prostate Cancer

Beyond detection of elevated PSA and other prostate cancer marker levels such as those disclosed herein, other current methods for diagnosing and staging PCA are known to medical practitioners skilled in the art and include rectal examination, transrectal ultrasonography (TRUS) or magnetic resonance imaging (MRI), bone scanning, X-rays, skeletal survey, intravenous pyelography, CAT-scan, and biopsy (reviewed in Garnick, M. (1993), *Annals of Internal Medicine*, 118:803-818; and Garnick, M. (1994), *Scientific American*, 270:72-81).

Digital Rectal Exam

In a "digital rectal exam" (DRE), a clinician uses a gloved finger to assess the posterior aspect of the prostate through the rectal wall. The clinician will check the rear surface of the prostate for abnormalities such as hardness, a lump, or an enlarged prostate. In an embodiment, the subject in the above diagnostic and prognostic assays of this invention was identified by a digital rectal exam as having a prostate abnormality.

ABCD Scale and TNM Staging System.

Prostate cancer (PCA) stages are commonly evaluated according to a scale divided as A, B, C and D. Tumors in stage A are microscopic; stage $A_1$ designates tumors confined to a relatively small area and composed of well-differentiated tissue; stage $A_2$ tumors are more diffuse and less well differentiated; stage B tumors are large enough to be felt during a rectal examination; and stage C prostate cancers have spread throughout the gland and typically have pushed past the borders of the prostate into surrounding structures. Stage D tumors have metastasized, e.g., to lymph nodes, bone, or other organs. Alternatively, tumors are also staged by the TNM staging system, in which tumors are ranked on a scale of progressively worsening disease from T1a to T4b (e.g., T1c tumors are non-palpable and non-visible that were detected by elevated blood levels of prostate specific antigen). The TNM system for staging prostate cancer is summarized in Table 3, which follows. Of tumors characterized as being in stages A2, B, or C, 25% to 50% turn out, on further testing, to be metastatic. Methods involving procedures for removal or destruction of prostatic tumor tissue usually are employed with non-metastasized cancers. For example, radical prostatectomy preferably is used with stage A, B and some stage C tumors (i.e., where the tumor growth has not extended considerably beyond the borders of the prostate gland) as well as stage T1c tumors. X-ray therapy (e.g., external or interstitial) preferably is used with stage A, B or C tumors as well as T1c tumors. Additional diagnostic tools might aid in distinguishing cases suitable for various treatments.

TABLE 3

The TMN System of Prostate Tumor Classification

| Classification | Description |
|---|---|
| | Incidental prostate cancer |
| TX | Primary tumour cannot be assessed |
| T0 | No evidence of primary tumour |
| T1 | Clinically unapparent tumour, not palpable nor visible by imaging |
| T1a | Tumour an incidental histological finding in 5% or less of tissue resected |
| T1b | Tumour an incidental histological finding in more than 5% of tissue resected |
| T1c | Tumour identified by needle biopsy (e.g. because of elevated serum PSA level) |
| | Palpable or visible carcinoma confined to the prostrate |
| T2* | Tumour confined within the prostate |
| T2a | Tumour involves half of a lobe or less |
| T2b | Tumour involves more than half a lobe but not both lobes |
| T2c | Tumour involves both lobes |
| | Locally extensive prostate cancer |
| T3** | Tumour extends through the prostate capsule |
| T3a | Unilateral extracapsular extension |
| T3b | Bilateral extracapsular extension |
| T3c | Tumour invades seminal vesicle(s) |
| | Locally extensive tumours with fixation or invasion into neighbouring organs |
| T4 | Tumour is fixed or invades adjacent structures other than seminal vesicles |
| T4a | Tumour invades bladder neck and/or external sphincter and/or rectum |
| T4b | Tumour invades levator muscles and/or is fixed to pelvic wall |

*Tumor found in one or both lobes by needle biopsy, not palpable or visible by imaging, is classified as T1c.
**Invasion into the prostatic apex or into (but not beyond) the prostatic capsule is not classified as T3 but as T2.

Gleason Scoring

Another commonly used system for determining the prognosis of a patient with prostate cancer is the Gleason scoring system. The "Gleason score" or "Gleason grade" is a value from 1 (well differentiated) to 5 (poorly differentiated) based on the examination of slices of prostate cancer tissue under a microscope. The lower the Gleason score the more the prostate cancer tissue resembles the structure of normal prostate tissue and the less aggressive the cancer is likely to be.

The "combined Gleason score" or "Gleason sum" is a value from 2 (least anaplastic) to 10 (most anaplastic) based on the Gleason scores of the 2 most common histological patterns in the prostate cancer tissue. The lower the Gleason sum, the better the prognosis for the patient. The most common Gleason sums are 6 and 7, which often represent a gray zone for cancer prognosis. Tables 4A-4D (the Partin Coefficient Tables), which follow, show the probability of organ-confined prostate cancer based on the PSA levels, Gleason score, and stage of the prostate cancer.

TABLE 4A

Prediction of Probability of Organ-Confined Disease (for PSA = 0.0-4.0 ng/ml)

| Gleason score | Stage T1a | Stage T1b | Stage T1c | Stage T2a | Stage T2b | Stage T2c | Stage T3a |
|---|---|---|---|---|---|---|---|
| 2-4 | 90 | 80 | 89 | 81 | 72 | 77 | — |
| 5 | 82 | 66 | 81 | 68 | 57 | 62 | 40 |
| 6 | 78 | 61 | 78 | 64 | 52 | 57 | 35 |
| 7 | — | 43 | 63 | 47 | 34 | 38 | 19 |
| 8-10 | — | 31 | 52 | 36 | 24 | 27 | — |

All numbers represent percent predictive probabilities (95% confidence interval); ellipses indicate lack of sufficient data to calculate probability

TABLE 4B

Prediction of Probability of Organ-Confined Disease (for PSA = 4.1-10.0 ng/ml)

| Gleason score | Stage T1a | Stage T1b | Stage T1c | Stage T2a | Stage T2b | Stage T2c | Stage T3a |
|---|---|---|---|---|---|---|---|
| 2-4 | 84 | 70 | 83 | 71 | 61 | 66 | 43 |
| 5 | 72 | 53 | 71 | 55 | 43 | 49 | 27 |
| 6 | 67 | 47 | 67 | 51 | 38 | 43 | 23 |
| 7 | 49 | 29 | 49 | 33 | 22 | 25 | 11 |
| 8-10 | 35 | 18 | 37 | 23 | 14 | 15 | 6 |

All numbers represent percent predictive probabilities (95% confidence interval); ellipses indicate lack of sufficient data to calculate probability

TABLE 4C

Prediction of Probability of Organ-Confined Disease (for PSA = 10.1-20.0 ng/ml)

| Gleason score | Stage T1a | Stage T1b | Stage T1c | Stage T2a | Stage T2b | Stage T2c | Stage T3a |
|---|---|---|---|---|---|---|---|
| 2-4 | 76 | 58 | 75 | 60 | 48 | 53 | — |
| 5 | 61 | 40 | 60 | 43 | 32 | 36 | 18 |
| 6 | — | 33 | 55 | 38 | 26 | 31 | 14 |
| 7 | 33 | 17 | 35 | 22 | 13 | 15 | 6 |
| 8-10 | — | 9 | 23 | 14 | 7 | 8 | 3 |

All numbers represent percent predictive probabilities (95% confidence interval); ellipses indicate lack of sufficient data to calculate probability

TABLE 4D

Prediction of Probability of Organ-Confined Disease (for PSA = >20.0 ng/ml)

| Gleason score | Stage T1a | Stage T1b | Stage T1c | Stage T2a | Stage T2b | Stage T2c | Stage T3a |
|---|---|---|---|---|---|---|---|
| 2-4 | — | 38 | 58 | 41 | 29 | — | — |
| 5 | — | 23 | 40 | 26 | 17 | 19 | 8 |
| 6 | — | 17 | 35 | 22 | 13 | 15 | 6 |
| 7 | — | — | 18 | 10 | 5 | 6 | 2 |
| 8-10 | — | 3 | 10 | 5 | 3 | 3 | 1 |

All numbers represent percent predictive probabilities (95% confidence interval); ellipses indicate lack of sufficient data to calculate probability The development of the prostate specific antigen (PSA) test as a diagnostic tool for prostate cancer has allowed the earlier and more accurate detection of clinical prostate carcinoma. Before the development of this test, most tumors were discovered by manual examination and these tumors were necessarily large and often high grade. A significant portion of these tumors were already metastatic. The advent of PSA test has enabled the detection of smaller tumors, the majority of which are intermediate grade (Gleason score 6-7).

Despite our increased ability to detect early prostate tumors, it is difficult, especially in patients with mid-grade tumors, to determine which patients will have an indolent disease course and which patients will go on to develop metastatic disease. The therapeutic decision of which patients should have aggressive treatment and which should have less aggressive treatment followed by PSA monitoring is particularly difficult to make for these mid-grade patients. The ability to distinguish the potential outcome of a particular tumor would potentially have a great effect on the selection of a treatment course for that patient. Therefore, the prognostic assays of this invention are also particularly useful when the Gleason sum falls within a gray zone where the prognosis is usually unclear (i.e. a Gleason sum of 6 or 7).

The invention is further illustrated by the following examples, which should not be construed as further limiting. The contents of all references, pending patent applications and published patents, cited throughout this application are hereby expressly incorporated by reference

EXAMPLES

Example 1

Primary Screen for Pin1 Expression in Human Tissues

Materials and Methods

Human Biological Samples

Formalin-fixed, paraffin-embedded sections of normal human organs were obtained from Novagen (Madison, Wis.). Organs examined included: prostate, brain, pituitary gland, kidney, muscle, esophagus, stomach, small intestines, colon, liver, spleen, pancreas, thyroid, heart, lung, bladder, adipose, lymph node, uterus, ovary, adrenal, testis, tonsil and thymus.

Formalin-fixed, paraffin-embedded sections of 19 different human tumor tissues were obtained from both Novagen and Imgenix (San Diego, Calif.). Cancers examined included: prostate, stomach, breast, pancreas, lung, liver, renal, ovary, thyroid, bladder, uterine cervix, colon, esophagus, lymphoma, endometrium, head/neck, gallbladder, melanoma, parotid.

Antibody

A commercial polyclonal antibody (Ab-1) (Oncogene Research Products, MA) was employed in this study, which was generated by immunizing rabbits with recombinant human Pin1. The specificity of the antibody was tested and confirmed by Western blotting and affinity purification.

Immunohistochemistry

Immunohistochemistry was performed on formalin-fixed tissues embedded in paraffin and sectioned at 4 to 6 μm for both normal and tumor tissues. The sections were deparaffinized in xylene, rehydrated in graded ethanols (100, 95 and 75%), followed by immersed in 3% H2O2/methanol for 15 minutes. For antigen retrieval, sections were microwaved in citrate buffer (pH 6.0) (BioGenex) for 15 minutes. Sections were then blocked in 10% normal goat serum in TBS, followed by incubation with primary antibody 1:800 overnight at 4° C. Incubation with biotinylated goat anti-rabbit antibody (Vector Laboratories, Burlingame, Calif.) for 30 minutes at room temperature was followed by the standard avidin-biotin-complex (ABC) process (Vectastain Elite ABC kit, Vector). Diaminobenzidine (DAB) was used as a chromogen, followed by counterstaining with hematoxylin. For negative controls, the primary antibody was omitted and prior immunostaining with preabsorbed antibody did not reveal any specific reactivity.

Results

Normal Tissues

Normal human biological samples from 25 organs were studies. In normal tissues, the Pin1 level was low except for normal kidney, brain, pancreatic islet cells and testis tissues where higher levels of Pin1 were detected.

Tumor Tissues 260 tumor samples from 19 different types of common human cancers were studied. All 19 different types of cancers have shown Pin1 over-expression. The incidence of Pin1 protein over-expression varies in different types of cancers (Table 5).

TABLE 5

Pin1 Expression in Human Tumors

| Tumor Type | Total number | % Positive |
|---|---|---|
| Prostate | 49 | 92% |
| Stomach | 18 | 28% |
| Breast | 17 | 100% |
| Pancreatic | 16 | 33% |
| Lung | 14 | 50% |
| Liver | 13 | 31% |
| Renal | 13 | 23% |
| Ovary | 12 | 58% |
| Thyroid | 12 | 58% |
| Bladder | 11 | 81% |
| Uterine Cervix | 11 | 73% |
| Colon | 11 | 55% |
| Esophagus | 11 | 55% |
| Malignant lymphoma | 10 | 90% |
| Endometrium | 10 | 90% |
| Head/Neck | 10 | 60% |
| Gallbladder | 10 | 45% |
| Malignant melanoma | 9 | 100% |
| Parotid | 3 | 33% |

Example 2

Use of Pin1 as a Prognostic Marker in Human Prostate Cancer

Materials and Methods

A total of 42 patients with prostatic adenocarcinoma underwent radical prostatectomy between 1988 and 1996. The clinical stage of the prostate tumor was assessed retrospectively by a review of the medical records. The grade of each neoplasm was determined using the Gleason scoring system.

Antibody

A commercially available human polyclonal Pin1 antibody (Oncogene Research Products, MA) was used in this study. The antibody was affinity-purified using CNBr-activated Sepharose 4B column (Amersham Pharmacia Biotech). The purified antibody was tested on a Western blot which contained recombinant human Pin1 protein.

Immunohistochemical Staining.

Human prostate cancer sections were stained for Pin1 using an avidin-biotin-peroxidase complex (ABC) method (Vector, Burlingame, Calif.). Formalin-fixed, paraffin-embedded 5 μm tissue sections were deparaffinized in xylenes, rehydrated in graded alcohols, and blocked for endogenous peroxidase activity by 3% hydrogen peroxide (Sigma) in methanol for 15 min. For antigen retrieval, sections were microwaved in citrate buffer, pH 6.0 (BioGenex) for 15 min. The sections were then treated with 10% normal serum same specie as secondary antibody for 40 min to prevent nonspecific binding before incubating with an anti Pin1 antibody overnight at 4° C. at 1:800 (v/v) dilution. The sections were washed 4 times (5 min each) with TBS followed by incubation with a biotinylated goat anti-rabbit IgG antibody for 40 min. After incubation with a preformed avidin-biotin complex for 40 min, specifically bound antibodies were visualized by using peroxidase substrate, 3,3'-diaminobenzidine tetrahydrochloride (DAB). Sections were counterstained with Gill's hematoxylin. Negative controls included sections without primary antibody or with normal serum instead of Pin1 antibody.

Discussion

Using affinity purified polyclonal Pin1 antibody, an immunohistochemical study on paraffin sections of 42 human prostate carcinoma cases was conducted. Positive immunostaining was observed in the cytoplasm as well as the nucleus of epithelial cells in neoplastic prostates but not in or very little in normal prostates. The stromal cells surrounding tumors showed no or very little Pin1 expression. Among the specimens investigated, well differentiated carcinomas with Gleason scores 4-5 generally showed no Pin1 staining or very low levels of staining. In some cases, high-grade prostatic interstitial neoplasia (PIN) showed Pin1 immunostaining, but usually to a lesser extent than the malignant lesions. Moderately differentiated prostate carcinomas with Gleason 6-7 showed partially positive immunostaining, in which not all cancer cells expressed Pin1, nor all cancerous lesions in a same specimen. Poorly differentiated prostate carcinomas with Gleason scores 8-10 displayed the most extensive and intense Pin1 immunoreaction.

Pin1 staining levels for all prostatic carcinoma specimens are summarized in FIG. 1. The results showed a general correlation between Pin1 expression and the Gleason scores, with high grade tumors (Gleason scores of 8-10) showing a higher percentage of positive staining than low grade (Gleason scores of 4-5) tumors. Interestingly, moderately differentiated prostate carcinomas with Gleason scores of 6-7 could be divided into three groups according to the levels of Pin1 expression. Group I: less than 30% of cancer cells in a whole section stained for Pin1; group II: 30-50% of cancer cells stained for Pin1; group III: more than 50% stained for Pin1. 8 out of 42 cases (19%) were classified as group I; 15 (36%) cases were classified as group II; and 19 (45%) were classified as group III.

Gleason grading system is the most common clinical practice for prostate cancer, with high Gleason scores showing high rate of recurrence and metastasis, and low Gleason scores showing low rate of mortality. Patients in intermediate grade (Gleason score 6-7) have various outcomes. Most people diagnosed as having prostate cancer belong to this group and present the biggest challenge to the diagnosing clinician. Patients in group I appear to represent an indolent disease course and have a low risk of developing metastatic disease; patients in group III are likely to go on to develop metastatic disease. Therefore, Pin1 staining of prostate cancer is a useful tool to measure the degree of biological aggressiveness of prostate cancer.

Clinical follow-up for three years or more on patients is summarized in Table 6. Prostate specific antigen (PSA) is commonly used for early diagnosis of prostate cancer and monitoring the effectiveness of treatment. After surgery, PSA level is undetectable. In the follow-up, if PSA level becomes detectable, it is called PSA failure that indicates either primary tumor recurrence or development of metastasis. Based on Pin1 expression and PSA follow-up, it was found that there is a tendency that at the time of surgery, patients whose tumor showed high levels of Pin1 expression were likely to experience PSA failure. Table 7 shows the correlation between Pin1 expression and PSA failure. Patients with low levels of Pin1 expression (0-30% of tumor cells positive) showed low rate of PSA failure (12.5%), followed by medium levels of Pin1 expression (30-50%) showing higher rate of failure (64%). Patients with high levels of Pin1 expression (50-100%) exhibited the highest rate of PSA failure (78%).

TABLE 6

Pin1 Expression and Clinical Outcome in Prostate Cancer

| | Pin1 Intensity | % Cells Expressing Pin1 | Gleason Sum | Surgery date | PSA Failure | PSA failure-Date |
|---|---|---|---|---|---|---|
| 1 | + | 50% | 7 | Sep. 9, 1991 | 1 | Aug. 24, 1992 |
| 2 | + | 50% | 4 | Jan. 24, 1992 | 0 | Mar. 30, 1995 |
| 3 | + | 80% | 7 | Aug. 17, 1992 | 0 | Sep. 16, 1992 |
| 4 | + | 90% | 10 | Oct. 20, 1992 | 1 | Jul. 1, 1993 |
| 5 | + | 40% | 7 | Nov. 11, 1992 | n/a | |
| 6 | ++ | 70% | 7 | Dec. 7, 1992 | 1 | Jul. 1, 1993 |
| 7 | + | 30% | 7 | Mar. 1, 1993 | 0 | Nov. 7, 1996 |
| 8 | + | 50% | 7 | May 14, 1993 | 0 | Aug. 8, 1996 |
| 9 | + | 60% | 7 | Sep. 28, 1993 | 1 | Jan. 12, 1995 |
| 10 | + | 70% | 8 | Nov. 7, 1994 | 1 | May 16, 1995 |
| 11 | + | 40% | 8 | Dec. 5, 1994 | 1 | Sep. 3, 1996 |
| 12 | ++ | 70% | 7 | Jan. 4, 1995 | 1 | Sep. 13, 1996 |
| 13 | + | 80% | 7 | Feb. 15, 1995 | 1 | Jul. 31, 1995 |
| 14 | + | 80% | 5 | Feb. 24, 1995 | 0 | Nov. 22, 1996 |
| 15 | + | 50% | 7 | Apr. 13, 1995 | 1 | Jun. 16, 1995 |
| 16 | + | 80% | 7 | Mar. 8, 1995 | 0 | May 21, 1997 |
| 17 | + | 30% | 7 | May 12, 1995 | 0 | Dec. 13, 1995 |
| 18 | + | 80% | 7 | May 9, 1995 | 0 | Oct. 24, 1996 |
| 19 | + | 40% | 7 | Sep. 22, 1995 | 0 | Apr. 11, 1997 |
| 20 | + | 80% | 8 | Jan. 29, 1996 | n/a | |
| 21 | ++ | 70% | 7 | Sep. 13, 1989 | 1 | Aug. 01, 1991 |
| 22 | + | 40% | 7 | Jan. 23, 1990 | 1 | Jul. 10, 1992 |
| 23 | ++ | 30% | 7 | Dec. 20, 1989 | 1 | Jul. 26, 1991 |
| 24 | + | 40% | 6 | Feb. 07, 1990 | 0 | 0 |
| 25 | + | 40% | 7 | May 6, 1988 | 0 | Feb. 11, 1993 |
| 26 | ++ | 70% | 9 | Nov. 17, 1988 | 1 | Sep. 10, 1990 |
| 27 | + | 40% | 7 | Feb. 13, 1990 | 1 | May 27, 1993 |
| 28 | ++ | 60% | 8 | Apr. 24, 1991 | 1 | Oct. 7, 1999 |
| 29 | + | 60% | 7 | Sep. 18, 1991 | 1 | May 12, 1995 |
| 30 | + | 50% | 7 | Oct. 21, 1991 | 0 | Oct. 25, 1999 |
| 31 | + | 50% | 6 | Oct. 25, 1991 | 1 | Jul. 16, 1992 |
| 32 | + | 30% | 5 | May 18, 1999 | 0 | Mar. 21, 1995 |
| 33 | + | 50% | 7 | Feb. 22, 1989 | 1 | Mar. 13, 1989 |
| 34 | + | 60% | 7 | Feb. 22, 1989 | 1 | Mar. 13, 1989 |
| 35 | + | 10% | 7 | May 24, 1989 | 0 | Jun. 14, 1999 |
| 36 | + | 70% | 7 | Jan. 2, 1990 | 0 | Jan. 17, 1992 |
| 37 | + | 50% | 7 | Feb. 16, 1990 | 1 | Nov. 15, 1990 |
| 38 | + | 70% | 7 | Nov. 8, 1990 | 1 | Sep. 11, 1991 |
| 39 | + | 60% | 7 | Dec. 14, 1990 | 1 | Sep. 27, 1995 |
| 40 | + | 50% | 7 | Feb. 27, 1991 | 1 | Jun. 11, 1992 |
| 41 | + | 10% | 6 | May 9, 1991 | 0 | Jul. 11, 1997 |
| 42 | + | 10% | 7 | Jul. 8, 1994 | 0 | Jul. 1, 1995 |

TABLE 7

Pin1 Expression and PSA Failure in Prostate Cancer

| % Pin1 positive cells | PSA Failure + | PSA Failure − | % |
|---|---|---|---|
| 0-30 | 1 | 7 | 12.5 |
| 30-50 | 9 | 5 | 64 |
| 50-100 | 14 | 4 | 78 |

As the above data show, patients with the most extensive Pin1 staining are at greater risk to develop recurrent disease than those with low Pin1 staining, and Pin1 can be used as a biomarker that functions as an indicator of metastatic progression and disease outcome in human prostate cancer patients.

Example 3

PIN 1 as a Prognostic Marker for Biochemical Failure

Materials and Methods

Study Subjects:

Over 3400 of patients with Benign Prostatic Hyperplasia (BPH) or cancer underwent radical prostatectomies at one of the Baylor College of Medicine affiliated institutions (The Methodist Hospital, Ben Taub Hospital, Saint Luke's Hospital and the Houston Veterans Affairs Medical Center), and provided tissues for the Baylor Prostate SPORE Tissue Bank in the Histology Core. Radical prostatectomy specimens from these patients were processed using whole mount slides according to procedures previously described by for example, Sakr, W. A., et al. (1996) Cancer 15; 78:366-778 or Ohori, M. et al. (1999) J. Urol. 161:500-4. Of these patients 1291 were operated by a single surgeon between 1983 and 1998 without any previous form of adjuvant therapy such as radiation or hormonal therapy. These are 87.9% Caucasians, 7.4% Hispanic, 3.5% African-American and 1.2% Asian or Middle Eastern. Complete demographic, clinical and follow-up data was available in the Medical Informatics Core and includes patient's age, blood PSA levels, clinical staging, and biopsy pathologic information. Entry criteria for the retrospective cohort study to create a radical prostatectomy 1) No preoperative treatment 2) Operated by a single surgeon between 1983 and 1998 3) Radical prostatectomy specimen in the tissue bank 4) Prostate cancer present in the surgical specimen and large enough to be cored for tissue microarrays. A total of 622 patients fulfilled the above mentioned criteria and were cored to produce a large outcomes array.

Radical Prostatectomy Specimens:

After surgery, the prostate specimens were sliced into 5 mm-thick tissue whole mount according to a procedure previously described by for example, Sakr, W. A., et al. (1996) Cancer 15; 78:366-778 or Ohori, M. et al. (1999) J. Urol. 161:500-4. The tissue slices were then fixed in 10% neutral buffered formalin and embedded in paraffin according to a routine procedure. A single pathologist following a standard protocol evaluated H & E stained whole mount sections from each specimen.

Cohort Enrollment and Follow-Up:

Data about the population of patients mentioned above have been accrued to using SPORE protocols and gathered in the Medical Informatics Core using the SPORE in Prostate Cancer Information System (SPIS). A single pathologist performed the pathologic analysis that includes staging, pathologic stage, margins, capsular penetration, seminal vesicle invasion, biopsy and prostatectomy primary and secondary Gleason grades, lymph node status, tumor volume and geographic location. The clinical and pathologic data of patients who meet the entry criteria is available for analysis with patient identifiers removed. Institutional Review Board approved consent forms were used to obtain assent from all patients.

Array Construction and Tissue Sections:

The index tumor, defined as the largest and/or highest Gleason cancer focus, was identified and mapped on the whole mount sections for each specimen. The tissue microarrays were built using a visual tissue arrayer (Beecher Instruments, Silver Spring, Md.). Previous studies indicate that triplicate 0.6 mm. punches reliably reproduce immunohistochemical marker study results of full sections of prostate, even for low expression markers such as Ki67. We therefore punched triplicate 0.6-millimeter cores of the areas with highest Gleason grade within the mapped index tumor and transferred them to a recipient block. Areas of normal peripheral zone away from the tumor were also circled as well as areas of BPH. Transition zone without BPH was selected in the absence of BPH. The circled areas were then transferred on to the blocks and triplicate 0.6 mm. cores were also obtained from the circled areas of normal peripheral zone and BPH. Internal controls were placed at a pre-established pattern throughout each one of the blocks in order to assess adequacy of the stain throughout the sections. Sausage internal controls, which included up to 10 different types of tissues within each 0.6-mm.—control core, were also placed with the standard controls.

The final tissue array set consisted of 15 blocks with 9 cores for every one of the 622 patients for a grand total of approximately 5500 cores. A database was built for every block produced, including the coordinates of each core and the area and case of origin. Five-μm sections from the array blocks and tissues were cut without use of the transfer tapes for immunostaining.

Immunohistochemistry:

Sections were deparaffinized and rehydrated. They were then heated in Antigen Retrieval Citra solution (pH6.0) (BioGenex San Ramon, Calif., Cat. #HK086-9K), with in an 1300 w microwave oven (Panasonic, Inverter, the Genius 1300W) for 2 minutes at full power level to bring the solution to boiling temperature. Once it starts boiling, immediately reduce the power level of microwave to 10% and continue heating the slides for 15 min. Endogenous peroxidase in sections was inactivated in 3% H2O2 for 10 min. The sections were then blocked in 3% normal horse serum in 0.2 M phosphate-buffered-saline (PBS) pH 7.4 and followed by incubation in a Pin1 polyclonal antibody (Oncogene Research Products, Cambridge, Mass., Cat. #PC270, 4 mg/ml) diluted at 1:10,000 in TBS overnight at 4° C. They were then processed following a standard avidin biotin complex (ABC) immunostaining procedure with an ABC kit (Vector Lab, CA). Immuno-reaction products were visualized in a 3,3'-diaminobenzidine/H2O2 solution. To verify the specificity of the immunoreactions, some sections were incubated either in PBS or in normal rabbit serum replacing for the PIN 1 antibody.

Digitizing:

Each slide was digitized twice, using different imaging systems. The BLISS automated imaging system was used to digitize the micorarray slides initially. It produces a high-resolution image of every micorarray dot, with information as to the dot coordinates on the microarray slide. These images were used at Baylor College of Medicine for visual semiquantitation and subsequent correlation with the clinical database.

The ChromaVision System (ChromVision Medical Systems, Inc., San Juan Capistrano, Calif.) was used to digitize the microarray slides and perform automated image analysis.

Quantitation of Immunohistochemstry:

PIN 1 immunostaining in normal prostate epithelium, BPH and prostate cancer were evaluated microscopically and by image analysis and recorded as percentage of PIN 1 positive cells and intensity of PIN 1 staining using automated image analysis and visual semiquantitation. Because of the triplicate nature of the arrays, three values were obtained for every measurement. The highest value and the average of the three values were considered for analysis, giving rise to 4 interpretative values: Intensity high (PIH), Intensity Average (PIA), Percentage High (P % H) and Percentage Average (P % A).

Automated image analysis: Automated image analysis: Each micro-histoarry section was scanned and images were captured using automated cellular imaging system (ACIS) (ChromaVision Medical Systems, Inc., San Juan Capistrano, Calif.) which combines automated microscopy and computerized image processing in analysis of multiple tissues on a single slide. In this study, ACIS was used to analyze micro tissue array sections on glass slides stained using a diaminodenzidine chromagen (DAB) and hematoxylin counterstain. Positive staining (brown color) as viewed by light microscope indicates the presence of the protein, and color intensity correlates directly with protein quantity (expression). The ACIS is able to recognize 255 levels of immunohistochemical staining intensity (0-255) and convert these to fractional scores for the selected individual areas. However, because the system is very sensitive the base limit on the threshold for the Generic DAB is pre-set at 30 by the manufacturer. Therefore, any intensity below 30, which would have to be an extremely light brown, was treated as 0 in this study. Entire immunostained tissue sections were scanned using the 4x objective and images were captured using the 10x objective. In this study, we used the intensity scoring and percent positive scoring (the percentage of brown divided by blue plus brown area) for entire individual tissue dot selected. The immunohistochemical staining was quantitated without knowledge of the pathologist's score.

Visual Semiquantitation: The percentage of positive cells (labeling rate %) was defined as follows: 0 when no cells stained; 1, 2 and 3 when up to 33%, 66% and 100% of the cells were immunoreactive. The labeling intensity(I) was semi-quantified where 0 defined as lack of staining, 1 weak but distinct staining, 2 moderate staining seen at medium power and 3 intense staining seen at low power Statistical Analysis:

Associations between clinical/pathological parameters and PIN 1 expressions were evaluated using Spearman correlation coefficient testing. For survival analysis, the end point used was defined as cancer biochemical recurrence, defined as serum PSA level higher than 0.4 ng/ml on two successive measurements (Hybritech, Inc., San Diego, Calif.). Time to recurrence was defined as the time interval between the date of surgery and the date of identification of biochemical recurrence. The predictive value of PIN 1 for recurrence-free survival were determined using the Kaplan-Meier actuarial analysis and the log rank test. Kaplan-Meier survival curves were constructed for PIN 1-positive and PIN 1-negative patients. The differences between the survival curves between groups were tested for statistical significance by the log-rank test. The Cox univariate and multivariate proportional hazard regression model was used to evaluate the HR (relative risk of recurrence). In the multivariate analysis, the models were adjusted for LN, Surgical Margins, SVI, Gleason grade, ECE, UICC, and Preoperative PSA levels. All analyses were performed with a statistical software (Power and Precision software by Biostat (PC Version, Englewood, N.J.).).

Results

Valid information was obtained from tumor specimens of 580 patients. Patient ages ranged from 37 to 80 years, with a median of 63 years. Follow-up information (median follow-up period, 61 months) was available from 578 patients, among whom 111 (19.2%) had recurred. Other clinical characteristics are seen in Table 8.

TABLE 8

| Clinical/Pathological Factors | N (%) | Intensity High mean (sd) | p value | Intensity Average mean (sd) | P value | % High mean (sd) | p value | % Average mean (sd) | p value |
| --- | --- | --- | --- | --- | --- | --- | --- | --- | --- |
| TNM stage | | | | | | | | | |
| T1 | 182 (31) | 70.7 (15.4) | 0.158 | 66.1 (13.5) | 0.172 | 24.7 (25.3) | 0.191 | 17.6 (19.5) | 0.229 |
| T2 | 356 (61) | 71.7 (16.7) | | 66.6 (16.3) | | 25.3 (25.0) | | 18.0 (19.8) | |
| T3 | 42 (7) | 74.6 (16.0) | | 70.4 (14.9) | | 31.0 (25.2) | | 23.3 (21.0) | |
| Gleason score | | | | | | | | | |
| 4-6 | 232 (40) | 71.5 (13.8) | 0.779 | 67.5 (12.5) | 0.949 | 24.1 (23.6) | 0.499 | 17.3 (18.8) | 0.611 |
| 7 | 300 (52) | 71.6 (16.8) | | 66.0 (15.9) | | 26.3 (26.0) | | 18.6 (20.3) | |
| 8-10 | 47 (8) | 72.6 (23.3) | | 68.0 (23.4) | | 27.8 (26.8) | | 21.0 (21.9) | |

TABLE 8-continued

| Clinical/Pathological Factors | N (%) | Intensity High mean (sd) | p value | Intensity Average mean (sd) | P value | % High mean (sd) | p value | % Average mean (sd) | p value |
|---|---|---|---|---|---|---|---|---|---|
| Extraprostatic extension | | | | | | | | | |
| Positive | 258 (45) | 72.0 (16.4) | 0.328 | 67.0 (16.2) | 0.396 | 25.9 (24.7) | 0.437 | 18.6 (19.4) | 0.429 |
| Negative | 322 (55) | 71.2 (16.1) | | 66.5 (14.7) | | 25.2 (25.5) | | 18.0 (20.1) | |
| Seminal vesicle invasion | | | | | | | | | |
| Positive | 72 (12) | 73.8 (15.3) | 0.175 | 68.7 (13.8) | 0.124 | 27.8 (25.5) | 0.269 | 20.6 (21.1) | 0.240 |
| Negative | 508 (88) | 71.3 (16.4) | | 66.4 (15.6) | | 25.2 (25.1) | | 17.9 (19.6) | |
| Lymph node metastasis | | | | | | | | | |
| Positive | 37 (3) | 73.3 (19.1) | 0.114 | 70.2 (17.6) | 0.031 | 32.7 (24.3) | 0..026 | 25.9 (22.0) | 0.011 |
| Negative | 543 (97) | 71.5 (16.5) | | 66.5 (15.2) | ($r^2 = 0.09$) | 25.0 (25.1) | ($r^2 = 0.09$) | 17.7 (19.6) | ($r^2 = 0.11$) |
| Surgical margin | | | | | | | | | |
| Positive | 86 (15) | 70.3 (19.2) | 0.581 | 63.9 (19.2) | 0.353 | 24.2 (23.8) | 0.730 | 16.6 (17.8) | 0.504 |
| Negative | 494 (85) | 71.8 (15.7) | | 67.2 (14.6) | | 25.7 (25.4 | | 18.6 (20.1) | |
| UICC Staging | | | | | | | | | |
| Age | 580 | | 0.330 | | 0.316 | | 0.456 | | 0.401 |
| Preop PSA | 564 | | 0.724 | | 0.985 | | 0.149 | | 0.173 |

Normal and BPH:

PIN 1 staining was nuclear and seen in normal prostate, prostate cancer and BPH in varying intensities and percentages. However, a trend towards PIN 1 over-expression was noted in prostate cancer as compared to normal prostatic epithelium and BPH (see Table 9).

TABLE 9

| Tumor % Average | 18.27 | 10.34 |
|---|---|---|
| Normal Intensity High | 66.6 | 65 |
| Normal % Average | 8.1 | 3.3 |

TABLE 9-continued

| BPH Intensity High | 61.5 | 60 |
|---|---|---|
| BPH % Average | 6.7 | 1.2 |

Univariate analysis demonstrates that only the PIN 1 average intensity value in BPH tissues was statistically significant, but was lost on multivariate analysis (Table 10). The data indicates that PIN 1 expression in normal or hyperplastic prostatic tissues cannot be used to predict biochemical failure in PCa.

TABLE 10

| | Descriptives | | | Cox Univarate |
|---|---|---|---|---|
| | N | Mean (SD) | Median (Range) | p-value |
| Intensity High Normal | 569 | 66.6 (13.8) | 65 (0-127) | 0.094 |
| Intensity Average Normal | 570 | 59.9 (15.4) | 61 (0-109.3) | 0.731 |
| % High Normal | 567 | 12.3 (15.5) | 6.03 (0-85.8) | 0.437 |
| % Average Normal | 566 | 8.1 (11.4) | 3.3 (0-63.5) | 0.349 |
| Intensity High BPH | 573 | 61.5 (14.7) | 60 (0-110) | 0.055 |
| Intensity Average BPH | 572 | 55.8 (16) | 57.7 (0-99.5) | 0.039 (HR = 0.99) |
| % High BPH | 574 | 10.4 (15.8) | 2.2 (0-74.9) | 0.903 |
| % Average BPH | 575 | 6.7 (10.9) | 1.2 (0-56.9) | 0.837 |

Prostate Cancer:

PIN 1 expression in prostate cancer is nuclear and seen between 0 and 91% of the cells, with a median of 18% and a mean of 10% of the cells.

A) Image Analysis

1) Correlation

Correlation with clinical and pathologic factors showed that PIN 1 expression was associated with lymph node metastasis and clinical staging. (see Table 8).

2) Survival Analysis:

Continuous measures "PIN 1 Intensity High" (PIH), "PIN 1% High" (P % H), "PIN 1% Average" (P % A) were significant predictors for time to PSA recurrence, while "PIN 1 Intensity Average" (PIA) was not significant, univariately (Table 11). This finding is not surprising, for intensity of staining is usually best associated with the areas of greatest intensity or hot spots. In the same vein, the average of percentage of immunoreactive cells is a better measure of labeling rate.

TABLE 11

Univariate and multivariate Analysis of PIN 1 as a Predictor of Biochemical Recurrence

| | Models | HR (95% CI) | p-value |
|---|---|---|---|
| | PIH | | |
| Univariate | PIH (continuous) | 1.015 (1.003, 1.026) | 0.0120 |
| | PIH (split at median) | 1.512 (1.034, 2.213) | 0.0331 |
| | PIH (split at 100) | 2.642 (1.554, 4.493) | 0.0003 |
| Mulivariate | PIH (split at 100) | 3.902 (2.215, 6.873) | <0.0001 |
| | LN | 3.385 (2.087, 5.489) | <0.0001 |
| | Margins | 3.201 (2.117, 4.839) | 0.0460 |
| | Seminal Vesicel Invasion (SVI) | 2.883 (1.827, 4.549) | <0.0001 |
| | Gleason | 2.161 (1.629 2.867) | 0.0090 |
| | Extra Prostatic Extension (ECE) | 2.119 (1.202, 3.733) | <0.0001 |
| | Clinical Stage (IUCC) | 1.166 (1.003, 1.356) | <0.0001 |
| | PreOpPSA | 1.019 (1.009, 1.03) | <0.0001 |
| | PIA | | |
| Univariate | PIA (continuous) | 1.011 (0.999, 1.024) | 0.0763 |
| | PIA (split at median) | 1.446 (0.991, 2.110) | 0.0557 |
| | PIA (split at 100) | 3.566 (1.655, 7.682) | 0.0012 |
| Mulivariate | PIA (split at 100) | 5.318 (2.335, 12.116) | 0.0001 |
| | LN | 3.265 (2.026, 5.263) | <0.0001 |
| | Margins | 3.278 (2.151, 4.198) | <0.0001 |
| | SVI | 2.671 (1.699, 3.660) | <0.0001 |
| | Gleason | 2.121 (1.598, 2.816) | <0.0001 |
| | ECE | 2.074 (1.175, 3.660) | 0.0119 |
| | UICC | 1.137 (0.976, 1.324) | 0.0982 |
| | PreOpPSA | 1.020 (1.010, 1.031) | 0.0002 |
| | P % H | | |
| Univariate | P % H (continuous) | 1.008 (1.001, 1.015) | 0.0221 |
| | P % H (split at median) | 1.554 (1.062, 2.273) | 0.0233 |
| | P % H (split at 70) | 2.013 (1.167, 3.47) | 0.0118 |
| Mulivariate | P % H (split at 70) | 3.357 (1.905, 5.916) | <0.0001 |
| | PreOpPSA | 1.020 (1.01, 1.031) | <0.0001 |
| | UICC | 1.152 (0.992, 1.338) | 0.0631 |
| | LN | 3.091 (1.916, 4.986) | <0.0001 |
| | ECE | 2.173 (1.233, 3.828) | 0.0072 |
| | SVI | 2.732 (1.736, 4.301) | <0.0001 |
| | Margins | 3.258 (2.145, 4.948) | <0.0001 |
| | Gleason | 2.269 (1.707 3.016) | <0.0001 |
| | P % A | | |
| Univariate | P % A (continuous) | 1.011 (1.003, 1.02) | 0.0088 |
| | P % A (split at median) | 1.587 (1.085, 2.322) | 0.0174 |
| | P % A (split at 60) | 2.896 (1.662, 5.172) | 0.0003 |
| Mulivariate | P % A (split at 60) | 2.708 (1.416, 5.179) | 0.0026 |
| | LN | 2.557 (1.568, 4.169) | 0.0002 |
| | Margins | 3.457 (2.249, 5.315) | <0.0001 |
| | SVI | 2.617 (1.662, 4.121) | <0.0001 |
| | Gleason | 2.112 (1.595 2.795) | <0.0001 |
| | ECE | 2.122 (1.205, 3.739) | 0.0092 |
| | UICC | 1.147 (0.987, 1.332) | 0.0744 |
| | PreOpPSA | 1.021 (1.01, 1.031) | 0.0001 |

Since all measures are not normally distributed, first the medians were tested as possible cutoffs. Conclusions remained the same as for continuous measures. Then the optimal cutoffs were identified for all four measures of PIN 1 and tested for ability to predict time to recurrence.

Figure 2:
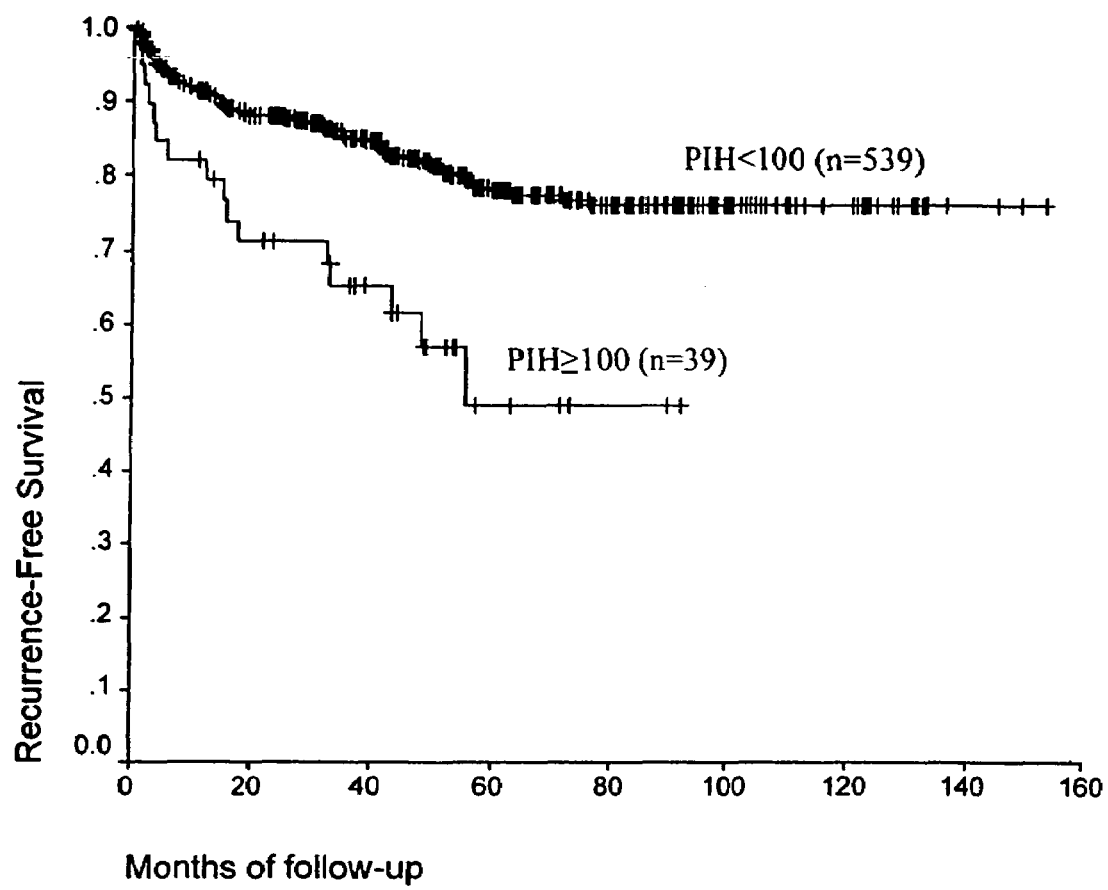
FIG. 2 shows the recurrence free survival as a function of time using Pin 1 High (P1H) intensity value of 100 as a cutoff between the two groups.
Figure 3:
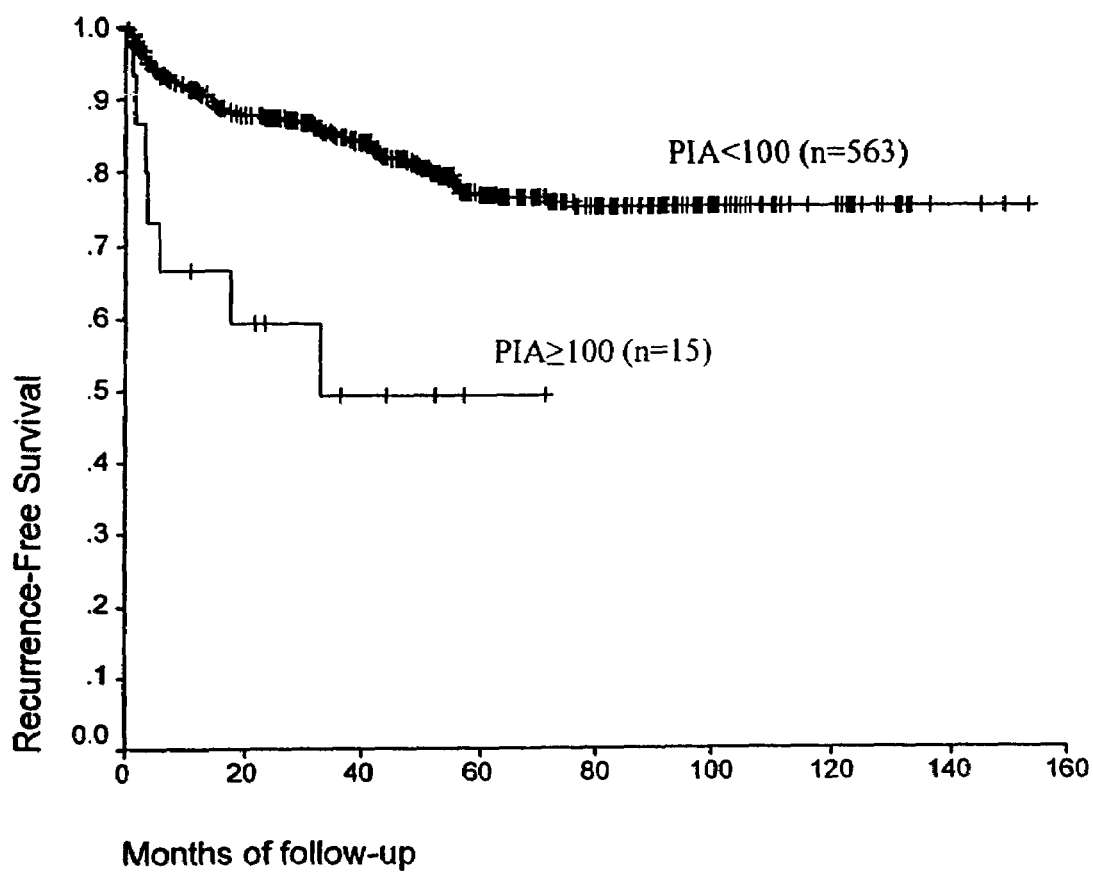
FIG. 3 shows the recurrence free survival as a function of time using Pin 1 Average (P1A) intensity value of 100 as a cutoff between the two groups.

PIH± were defined as "PIN 1 Intensity High" <100 and "PIN 1 Intensity High"≧100. The hazard ratio for PIH± was 2.6 (1.6,4.5) with p-value=0.0003 (FIG. 2). The cutoff of 100 was also used for PIA±, and the hazard ratio was 3.6 (1.7,7.7) with p-value=0.0012 (FIG. 3).

Figure 4:
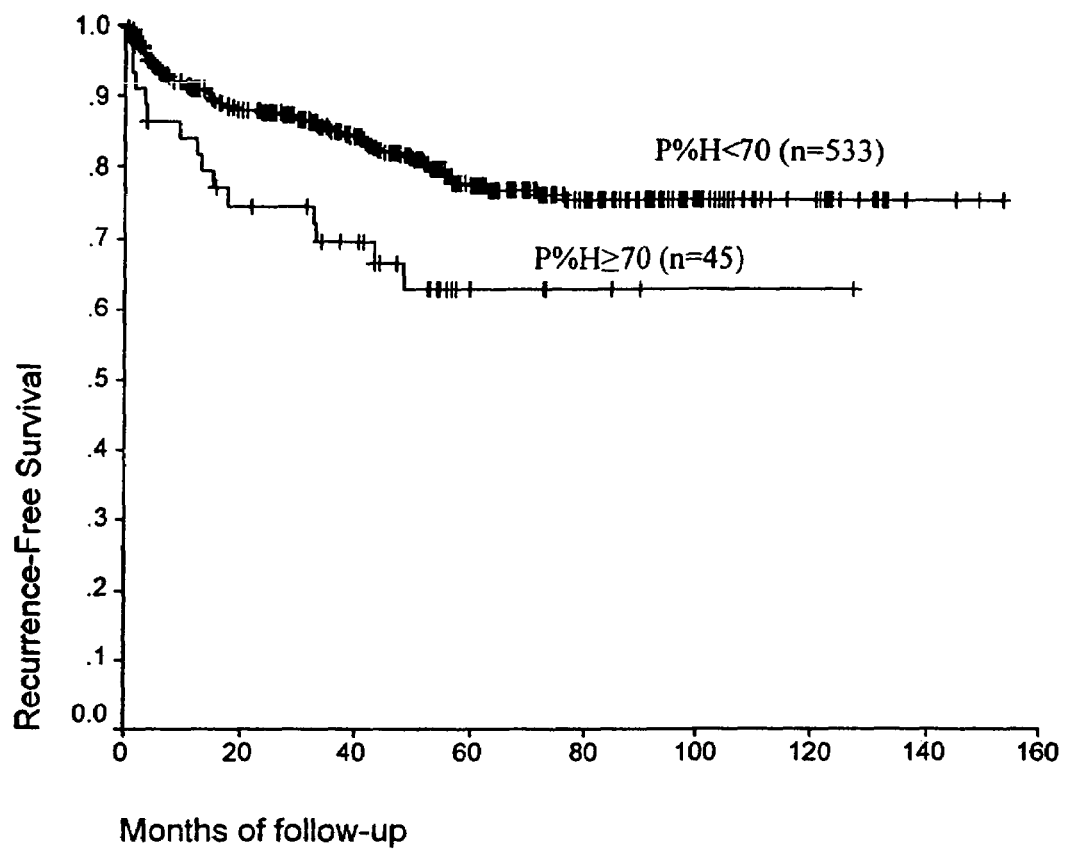
FIG. 4 shows the recurrence free survival as a function of time using Pin % High (P % H) intensity of value of 70 as a cutoff between the two groups.
Figure 5:
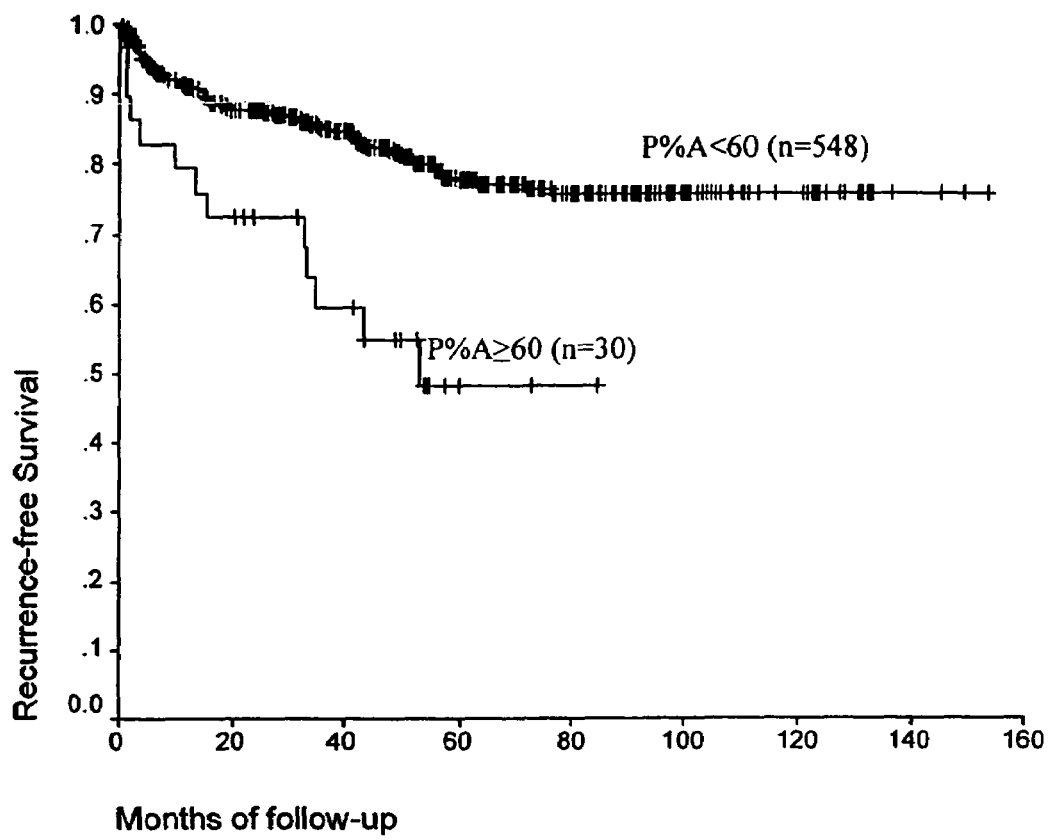
FIG. 5 shows the recurrence free survival as a function of time using Pin % Average (P % A) intensity of value of 60 as a cutoff between the two groups.

For "PIN 1% High" and "PIN 1% Average", cutoffs of 70 and 60 were used respectively. Both P % H± [HR=2.0(1.2, 3.5)] (FIG. 3) and P % A± [2.9(1.7, 5.2)] (FIG. 4) were significant predictors for time to recurrence (p=0.0118 and p=0.0003).

Kaplan-Meier survival curves (Table 8) also demonstrate that patients with PIN 1-positive tumors have substantially shorter time to recurrence compared with those who are PIN 1-negative.

In multivariate models these relationships were adjusted for LN, Surgical Margins, SVI, Gleason grade, ECE, UICC, and Preoperative PSA levels. All four discrete measures were shown to be significant independent predictors. Hazard ratios (Table 8) show that PIN 1 is as good, and possible much better, predictor for recurrence as these commonly used markers.

3) Gleason 6 and 7 Patients

Figure 6:
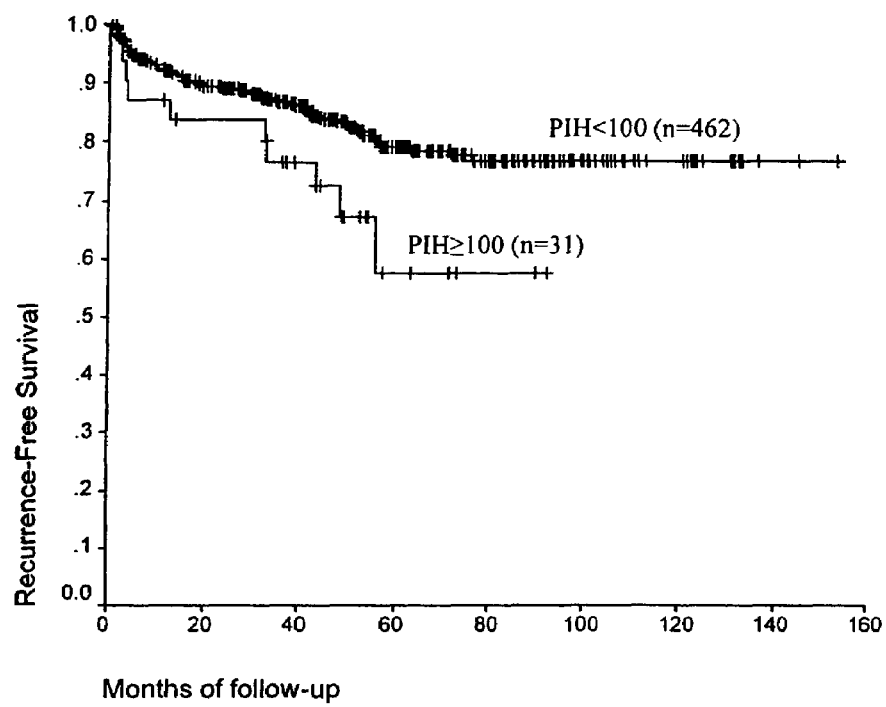
FIG. 6 depicts a multivariate analysis of Pin 1 as a marker of biochemical recurrence in Gleason 6 and 7 patients using a PIH score of 100 as a cutoff between the two groups.

PIH± was also tested in the subgroup of patients with Gleason grade 6-7. While the majority of PCA cancer patients falls into this category, this group of patients represents the most difficult predictive category in PCA. Currently there are no markers that will predict biochemical recurrence, metastasis or death. Univariately, PIN 1 remain a strong predictor of biochemical recurrence in this category of patients, with a p value of 0.0356 and a hazard ratio of 2.6 (1.6,4.5). The later increases on multivariate analysis to 3.4 (1.7,6.9), among the highest (FIG. 6). This data strongly suggests that PIN 1 status remains a strong significant and independent predictor for time to recurrence in this difficult group of patients with prostate cancer.

B) Visual Semiquantitation

Figure 7:
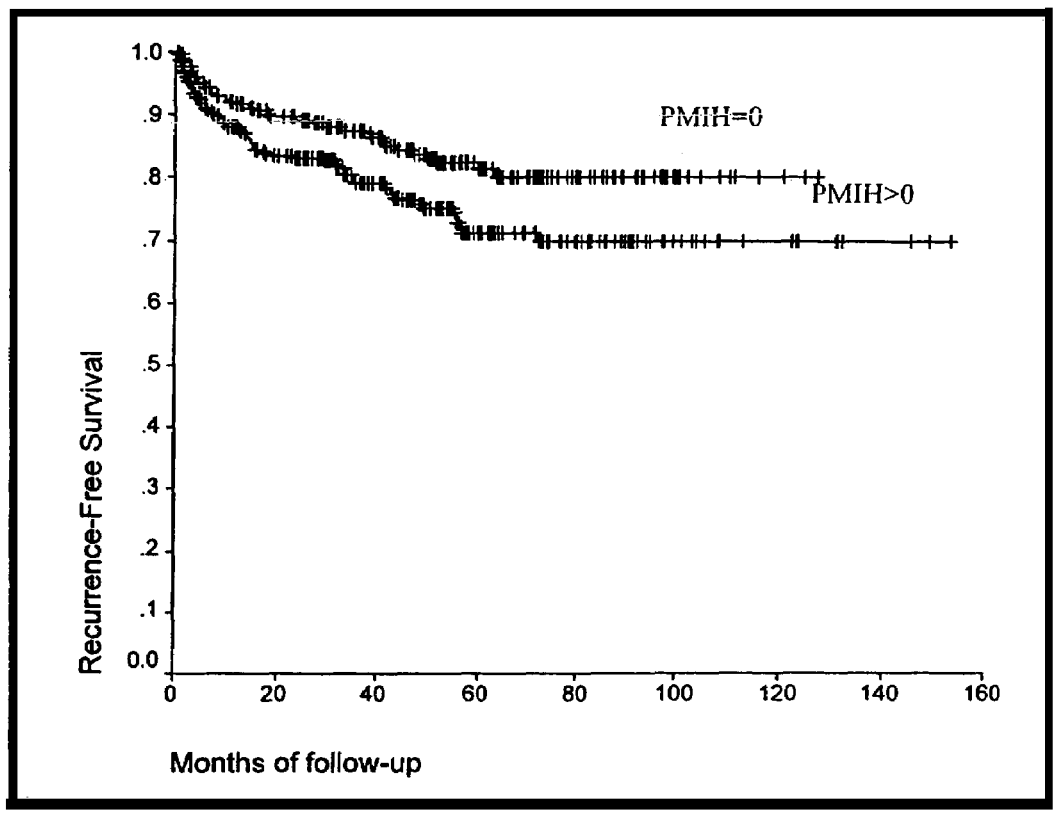
FIG. 7 depicts analysis of recurrence free survival as a function of time using visual Pin1 Intensity High (PMIH) values of 0 and >0 as a cutoff between the two groups.

PIN 1 expression was identified in 57.5% of the patients examined by visual semiquantitation, with the vast majority of these being low expressers (256 of 322). The human eye was not able to discriminate intensity of expression as well as the image analysis, for the results indicate significance only as an on/off phenomenon. The presence of stain, regardless of intensity, was a significant predictor of biochemical recurrence. While only 37 of 238 patients with no expression recurred, 72 of 307 patients with expression recurred, for a hazard ration of 1.6 on univariate and 1.9 (1.3-3.0) on multivariate analysis (FIG. 7).

When PIN 1 is expressed in PCA, the majority of the cancer cells were immunoreactive, with over 50% of the cases having immunoreactivity in 100% of the cells. Percent Positive Tumor was a significant continuous predictor (HR=1.004 p=0.0343) of time to recurrence. As the result of the optimal cutoff chosen at 10%, the division of patients 100% agreed with the Intensity Method described above. This cutoff is substantially lower than the one obtained by image analysis. It is important to stress however, that this technique measures the percent of cancer cells expressing PIN 1 while image analysis measures the percentage of the core that is immunoreactive.

Percent Positive in Core (<90% Vs 90-100) appeared to be a significant predictor of time to recurrence on the univariate analysis (p<0.0001), but when adjusted for know clinical and pathological predictors in a multivariate model, it was no longer significant (p=0.7242)

C) Correlation Between Visual and Image Analysis Results

There was a highly significant correlation between visual and machine measures. Although correlation coefficients were relatively low (Table 12), we believe that is due to the much more discrete nature of visual measurements.

TABLE 12

Correlation Between Visual and Image Analysis

| Machine | Visual Intensity in Tumor | | Visual % Positive in Tumor | |
|---|---|---|---|---|
| | rho | p-value | rho | p-value |
| Intensity High in Tumor | 0.4382 | <0.0001 | 0.4247 | <0.0001 |
| Intensity Average in Tumor | 0.4294 | <0.0001 | 0.4068 | <0.0001 |
| % High in Tumor | 0.3265 | <0.0001 | 0.3192 | <0.0001 |
| % Average in Tumor | 0.3347 | <0.0001 | 0.3220 | <0.0001 |

CONCLUSIONS

The data here presented establishes PIN 1 as an excellent prognostic marker for biochemical failure in prostate cancer patients treated with radical prostatectomy. The association of elevated PIN 1 expression with cancer's lymph node metastasis and clinical staging as well as poor clinical outcome indicates its involvement in disease progression.

The visual studies tell us that any intensity of expression of PIN 1 by a minority of Pca cells (>10%) is a very strong predictor of biochemical recurrence in patients with PCA. Although the results of visual and automated image analysis are significantly correlated, the higher hazard ratios obtained with the latter demonstrate a greater discriminatory power. It is apparent that image analysis is able to discriminate different intensities of expression and that a cutoff value can be used to determine groups with different survival. The patients with intensities over 100 have a higher rate of biochemical recurrence.

These results clearly indicate that PIN 1 can be used on radical prostatectomy specimens. We suggest that visual observation of labeling ratio, coupled with the enhanced discriminatory power of measuring intensity of expression by image analysis can be used to discriminate biochemical recurrence in patients that have undergone radical prostatectomies. Furthermore, because tissue microarray cores have similar amounts of tissue than biopsies, we are very hopeful that PIN 1 will have applications in pre therapy biopsies. If so, PIN 1 could be used to triage patients into watchful waiting with grater certainty.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method of determining the likelihood of prostate cancer recurrence in a subject comprising,
   providing a biological sample from the subject comprising prostate cancer cells characterized as having a Gleason score of 6 to 7; and
   determining the percentage of prostate cancer cells expressing detectable levels of Pin1 polypeptide in the sample by detecting the binding of an antibody that specifically binds to a Pin1 polypeptide consisting of the amino acid sequence set forth in SEQ ID NO: 1, or an antigen binding fragment thereof,
   wherein the percentage of prostate cancer cells in the sample positive for antibody binding is indicative of the likelihood of prostate cancer recurrence in the subject.

2. The method of claim 1, wherein a percentage of prostate cancer cells positive for antibody binding of less that 30% is indicative that the likelihood of prostate cancer recurrence in the subject is less than about 12.5%.

3. The method of claim 1, wherein a percentage of cells positive for antibody binding of 30-50% is indicative that the likelihood of prostate cancer recurrence in the subject is greater than about 12.5% and less than about 64%.

4. The method of claim 1, wherein a percentage of cells positive for antibody binding of greater than 50% is indicative that the likelihood of prostate cancer recurrence in the subject greater than about 64%.

5. A method of determining the likelihood of PSA failure in a subject following prostate surgery comprising,
   providing a biological sample from the subject at the time of the surgery comprising prostate cancer cells; and
   determining the percentage of prostate cancer cells expressing detectable levels of Pin1 polypeptide in the sample by detecting the binding of an antibody that specifically binds to a Pin1 polypeptide consisting of the amino acid sequence set forth in SEQ ID NO: 1, or an antigen binding fragment thereof,
   wherein the percentage of prostate cancer cells in the sample positive for antibody binding is indicative of the likelihood of PSA failure in the subject.

6. The method of claim 5, wherein a percentage of cells positive for antibody binding of less that 30% is indicative that the likelihood of PSA failure in the subject is less than about 12.5%

7. The method of claim 5, wherein a percentage of cells positive for antibody binding of between about 30-50% is indicative that the likelihood of PSA failure in the subject is between about 12.5% and about 64%.

8. The method of claim 5, wherein a percentage of cells positive for antibody binding of greater than about 50% is indicative that the likelihood of PSA failure in the subject is greater than about 64%.

* * * * *

SEQUENCE LISTING

<160> NUMBER OF SEQ ID NOS: 1

<210> SEQ ID NO 1
<211> LENGTH: 163
<212> TYPE: PRT
<213> ORGANISM: Homo sapiens

<400> SEQUENCE: 1

```
Met Ala Asp Glu Glu Lys Leu Pro Pro Gly Trp Glu Lys Arg Met Ser
 1               5                  10                  15

Arg Ser Ser Gly Arg Val Tyr Tyr Phe Asn His Ile Thr Asn Ala Ser
                20                  25                  30

Gln Trp Glu Arg Pro Ser Gly Asn Ser Ser Ser Gly Gly Lys Asn Gly
            35                  40                  45

Gln Gly Glu Pro Ala Arg Val Arg Cys Ser His Leu Leu Val Lys His
        50                  55                  60

Ser Gln Ser Arg Arg Pro Ser Ser Trp Arg Gln Glu Lys Ile Thr Arg
65                  70                  75                  80

Thr Lys Glu Glu Ala Leu Glu Leu Ile Asn Gly Tyr Ile Gln Lys Ile
                85                  90                  95

Lys Ser Gly Glu Glu Asp Phe Glu Ser Leu Ala Ser Gln Phe Ser Asp
            100                 105                 110
```

-continued

```
Cys Ser Ser Ala Lys Ala Arg Gly Asp Leu Gly Ala Phe Ser Arg Gly
        115                 120                 125

Gln Met Gln Lys Pro Phe Glu Asp Ala Ser Phe Ala Leu Arg Thr Gly
    130                 135                 140

Glu Met Ser Gly Pro Val Phe Thr Asp Ser Gly Ile His Ile Ile Leu
145                 150                 155                 160

Arg Thr Glu
```